US008344105B2

(12) United States Patent
Sato et al.

(10) Patent No.: US 8,344,105 B2
(45) Date of Patent: Jan. 1, 2013

(54) POLYPEPTIDES HAVING DNA POLYMERASE ACTIVITY

(75) Inventors: Yoshimi Sato, Otsu (JP); Kazue Nishiwaki, Otsu (JP); Nana Shimada, Otsu (JP); Shigekazu Hokazono, Otsu (JP); Takashi Uemori, Otsu (JP); Hiroyuki Mukai, Otsu (JP); Ikunoshin Kato, Otsu (JP)

(73) Assignee: Takara Bio Inc., Otsu-Shi (JP)

( * ) Notice: Subject to any disclaimer, the term of this patent is extended or adjusted under 35 U.S.C. 154(b) by 0 days.

(21) Appl. No.: 13/239,981

(22) Filed: Sep. 22, 2011

(65) Prior Publication Data

US 2012/0083590 A1 Apr. 5, 2012

Related U.S. Application Data

(62) Division of application No. 12/708,111, filed on Feb. 18, 2010, now Pat. No. 8,048,987, which is a division of application No. 11/628,268, filed as application No. PCT/JP2005/008711 on May 12, 2005, now Pat. No. 7,704,713.

(30) Foreign Application Priority Data

Jun. 4, 2004 (JP) .................................. 2004-166541

(51) Int. Cl.
*C12Q 1/68* (2006.01)
*C12P 19/34* (2006.01)
*C07K 1/00* (2006.01)
(52) U.S. Cl. ........ 530/350; 435/6.1; 435/6.11; 435/6.12
(58) Field of Classification Search ........................ None
See application file for complete search history.

(56) References Cited

U.S. PATENT DOCUMENTS

| 5,436,149 A | 7/1995 | Barnes |
| 5,489,523 A | 2/1996 | Mathur |
| 5,545,552 A | 8/1996 | Mathur |
| 5,866,395 A | 2/1999 | Mathur |
| 5,948,663 A | 9/1999 | Mathur |
| 6,008,025 A | 12/1999 | Komatsubara et al. |
| 6,054,301 A | 4/2000 | Kitabayashi et al. |
| 6,107,038 A * | 8/2000 | Choudhary et al. ......... 435/6.12 |
| 6,225,065 B1 | 5/2001 | Kitabayashi et al. |
| 6,489,150 B1 | 12/2002 | Mathur |
| 2002/0076768 A1 | 6/2002 | Kuroita et al. |
| 2004/0005599 A1 | 1/2004 | Schoenbrunner et al. |
| 2005/0069887 A1 | 3/2005 | Kitabayashi et al. |
| 2010/0173365 A1 | 7/2010 | Borns .......................... 435/91.2 |

FOREIGN PATENT DOCUMENTS

| EP | 0 822 256 A2 | 2/1998 |
| EP | 0834570 | 4/1998 |
| EP | 0962526 | 12/1999 |
| EP | 1154017 A1 | 11/2001 |
| EP | 1350841 | 10/2003 |
| JP | 7-298879 | 11/1995 |
| WO | WO 98/14590 | 4/1998 |
| WO | 0132887 A1 | 5/2001 |
| WO | 03/042383 A1 | 5/2003 |
| WO | 03054139 A2 | 7/2003 |

OTHER PUBLICATIONS

English translation of the Office Action issued in the corresponding Korean Patent Application No. 10-2009-7023784 issued on Feb. 22, 2010.
English translation of the Office Action issued in the corresponding Korean Patent Application No. 10-2009-7023787 issued on Feb. 22, 2010.
English translation of the Office Action issued in the corresponding Chinese Patent Application No. 200580026513.9 mailed on Mar. 2, 2010.
GenBank Accession No. U47108, Feb. 19, 2010.
Japanese and English translation of Office Action issued in the corresponding Japanese Patent Application No. 2006-514060 dated Jul. 6, 2010.
English translation of the Office Action issued in the corresponding Japanese Patent Application No. 2006-514060 mailed on Oct. 5, 2010.
M. W. Southworth et al., "Cloning of Thermostable DNA Polymerases From Hyperthermophilic Marine Archaea With Emphasis on *Thermococcus* sp. 9° N-7 and Mutations Affecting 3'-5' Exonuclease Activity" Pro. Natl. Acad. Sci., USA, May 1996, vol. 93, No. 11, pp. 5281-5285.
Wayne M. Barnes, "PCR Amplification of Up to 35-KB DNA With High Fidelity and High Yield From a Bacteriophage Templates", Proc. Natl. Acad. Sci., USA, Mar. 1994 vol. 91, pp. 2216-2220.
M. Takagi et al., "Characterization of DNA Polymerase From *Pyrococcus* sp. Strain KOD1 and Its Application to PCR", Applied and Environmental Microbiology, Nov. 1997, vol. 63, No. 11, pp. 4504-4510.
Taiwan Patent Office, Official Action, mailed Dec. 31, 2010 in Taiwan Patent Application No. 094118437.

* cited by examiner

*Primary Examiner* — Young J Kim
(74) *Attorney, Agent, or Firm* — Browdy and Neimark, P.L.L.C.

(57) ABSTRACT

A polypeptide having a high fidelity DNA polymerase activity and thus being useful as a genetic engineering reagent; a gene encoding this polypeptide; a method of producing the polypeptide; and a method of amplifying a nucleic acid by using the polypeptide.

10 Claims, 1 Drawing Sheet

POLYPEPTIDES HAVING DNA POLYMERASE ACTIVITY

CROSS-REFERENCE TO RELATED APPLICATIONS

This is a divisional of application Ser. No. 11/628,268, filed Dec. 4, 2006, which is a national phase of international application POT/JP05/08711, filed May 12, 2005. The entire contents of the prior applications are hereby incorporated by reference.

TECHNICAL FIELD

The present invention relates to a polypeptide having a high-fidelity DNA polymerase activity which is useful as a reagent for genetic engineering, a gene encoding the polypeptide, a method for producing the polypeptide, and a method for amplifying a nucleic acid using the polypeptide.

BACKGROUND ART

DNA polymerases are enzymes that are useful as reagents for genetic engineering and widely utilized for DNA sequencing, labeling, site-directed mutagenesis and the like. Thermostable DNA polymerases have lately attracted attention due to the development of the polymerase chain reaction (PCR) method. Various DNA polymerases suitable for the PCR method have been developed and put on the market.

Currently known DNA polymerases can be generally classified into four families based on the amino acid sequence similarities. Among them, the family A (pol I-type enzymes) and the family B (α-type enzymes) constitute a large majority. DNA polymerases belonging to each one of the families have generally similar biochemical characteristics. However, detailed comparison has revealed that the respective enzymes have properties different from each other in the substrate specificity, the incorporation of a substrate analog, the strength and velocity of primer extension ability, the mode of DNA synthesis, the accompaniment of an exonuclease activity, the optimal reaction conditions (temperature, pH, etc.), the sensitivity to inhibitors or the like. Thus, a DNA polymerase having the most suitable properties for the experimental procedure has been chosen from the existing ones and utilized.

For example, the DNA polymerase derived from *Pyrococcus furiosus* (Pfu) (see, for example, Patent Documents 1 to 5) is one of the most thermostable DNA polymerases. It has a 3'>5' exonuclease activity, which is known as a proofreading activity, and it exhibits relatively high fidelity among thermostable enzymes. However, this enzyme have problems that it requires a long time for amplification if it is used for PCR, and it cannot be used for amplification of a long chain because its extension velocity and processivity are low.

Recently, a polymerase called KOD DNA polymerase which has a higher 3'>5' exonuclease activity, a higher extension velocity and a higher processivity than the Pfu-derived DNA polymerase is commercially available (see, for example, Patent Documents 6 and 7, Non-patent Document 1). It is possible to carry out PCR with high accuracy in a short time using this enzyme. However, this enzyme has problems that it is relatively difficult to determine the reaction conditions because primers or amplification products are degraded due to the strong 3'>5' exonuclease activity, and it is not suitable for amplification of a long chain.

Furthermore, two types of enzymes have been developed by improving KOD DNA polymerase. One of them, KOD-Plus-DNA polymerase, enables hot-start PCR without a special procedure by adding two monoclonal antibodies to KOD DNA polymerase to suppress the polymerase activity and the 3'>5' exonuclease activity at normal temperature. The amplification efficiency and the ability of synthesizing a long-chain DNA are increased by optimizing the reaction buffer composition as compared with KOD DNA polymerase while retaining the high fidelity (e.g., Patent Document 8). However, there is a problem that the extension velocity of this enzyme is considerably lower than that of KOD DNA polymerase and is lowered to a level equivalent to that of the Pfu-derived DNA polymerase.

KOD Dash DNA polymerase is a mixture-type DNA polymerase prepared based on the method of Barnes et al. (see, for example, Patent Document 9, Non-patent Document 2). The amplification efficiency and the extension ability are increased by mixing KOD DNA polymerase and a modified type of KOD DNA polymerase from which the 3'>5' exonuclease activity has been eliminated using genetic engineering techniques at an optimal ratio (see, for example, Patent Document 10). Its extension velocity is high like KOD DNA polymerase. However, there is a problem that the fidelity is remarkably decreased as compared with KOD DNA polymerase alone because the 3'>5' exonuclease activity is relatively decreased.

Patent Document 1: U.S. Pat. No. 5,489,523
Patent Document 2: U.S. Pat. No. 5,545,552
Patent Document 3: U.S. Pat. No. 5,866,395
Patent Document 4: U.S. Pat. No. 6,489,150
Patent Document 5: U.S. Pat. No. 5,948,663
Patent Document 6: U.S. Pat. No. 6,054,301
Patent Document 7: U.S. Pat. No. 6,225,065
Patent Document 8: United States Patent Publication No. 2002/0076768
Patent Document 9: U.S. Pat. No. 5,436,149
Patent Document 10: U.S. Pat. No. 6,008,025
Non-patent Document 1: Barnes W. M., Proc. Natl. Acad. Sci. USA, vol. 91, No. 6, p. 2216-2220 (1994)
Non-patent Document 2: Takagi M., et al., Appl. Environ. Microbiol., vol. 63, No. 11, p. 4504-4510 (1997)

DISCLOSURE OF INVENTION

Problems to be Solved by the Invention

The main object of the present invention is to provide a polypeptide having a high-fidelity DNA polymerase activity which is useful for cloning, sequencing and nucleic acid amplification, and a gene encoding the polypeptide. Another object of the present invention is to provide a method for producing the polypeptide having a DNA polymerase activity and a method for amplifying a nucleic acid using the polypeptide having a DNA polymerase activity.

Means to Solve the Problems

As a result of intensive studies, the present inventors have found a novel polypeptide having a DNA polymerase activity, which has properties superior to any other conventional DNA polymerases, from a hyperthermophilic archaebacterium of the genus *Thermococcus*. Furthermore, the present inventors have cloned a gene encoding a polypeptide having such an activity and found a method for producing the polypeptide. Thus, the present invention has been completed.

The first aspect of the present invention relates to a polypeptide having a DNA polymerase activity, which has an amino acid sequence selected from the group consisting of the following or an amino acid sequence in which one or several amino acids are deleted, inserted, added or substituted in said amino acid sequence:
(a) the amino acid sequence of SEQ ID NO:16;
(b) the amino acid sequence of SEQ ID NO:24; and
(c) the amino acid sequence of SEQ ID NO:32.

The second aspect of the present invention relates to a nucleic acid encoding the polypeptide of the first aspect.

The nucleic acid of the second aspect may be a nucleic acid having the nucleotide sequence of SEQ ID NO:15, 23 or 31, or a part thereof. It may be a nucleic acid encoding a polypeptide having a DNA polymerase activity, which hybridizes to a nucleic acid consisting of a nucleotide sequence complementary to the above-mentioned nucleic acid under stringent conditions.

The third aspect of the present invention relates to a method for producing a polypeptide, the method comprising:
culturing a cell capable of producing a polypeptide, and collecting said polypeptide from the culture,
wherein said polypeptide has a DNA polymerase activity, and has an amino acid sequence selected from the group consisting of the following or an amino acid sequence in which one or several amino acids are deleted, inserted, added or substituted in said amino acid sequence:
(a) the amino acid sequence of SEQ ID NO:16;
(b) the amino acid sequence of SEQ ID NO:24; and
(c) the amino acid sequence of SEQ ID NO:32.

The fourth aspect of the present invention relates to a method for amplifying a nucleic acid, the method comprising:
amplifying a nucleic acid using a polypeptide,
wherein said polypeptide has a DNA polymerase activity, and has an amino acid sequence selected from the group consisting of the following or an amino acid sequence in which one or several amino acids are deleted, inserted, added or substituted in said amino acid sequence:
(a) the amino acid sequence of SEQ ID NO:16;
(b) the amino acid sequence of SEQ ID NO:24; and
(c) the amino acid sequence of SEQ ID NO:32.

The fifth aspect of the present invention relates to a composition which contains the polypeptide of the first aspect.

The sixth aspect of the present invention relates to a kit which contains the polypeptide of the first aspect.

The seventh aspect of the present invention relates to an antibody which binds to the polypeptide of the first aspect.

Effects of the Invention

The present invention provides a polypeptide having a high-fidelity DNA polymerase activity which is useful for cloning, sequencing and nucleic acid amplification, and a gene encoding the polypeptide, as well as a method for producing the polypeptide having a DNA polymerase activity. Using the polypeptide having a DNA polymerase activity of the present invention, it is possible to obtain an amplification product with a less error rate even if it is used in PCR comprising many cycles, for example. Thus, it is useful for analysis or identification of a target nucleic acid present at low copy number.

BEST MODE FOR CARRYING OUT THE INVENTION

Figure 1:
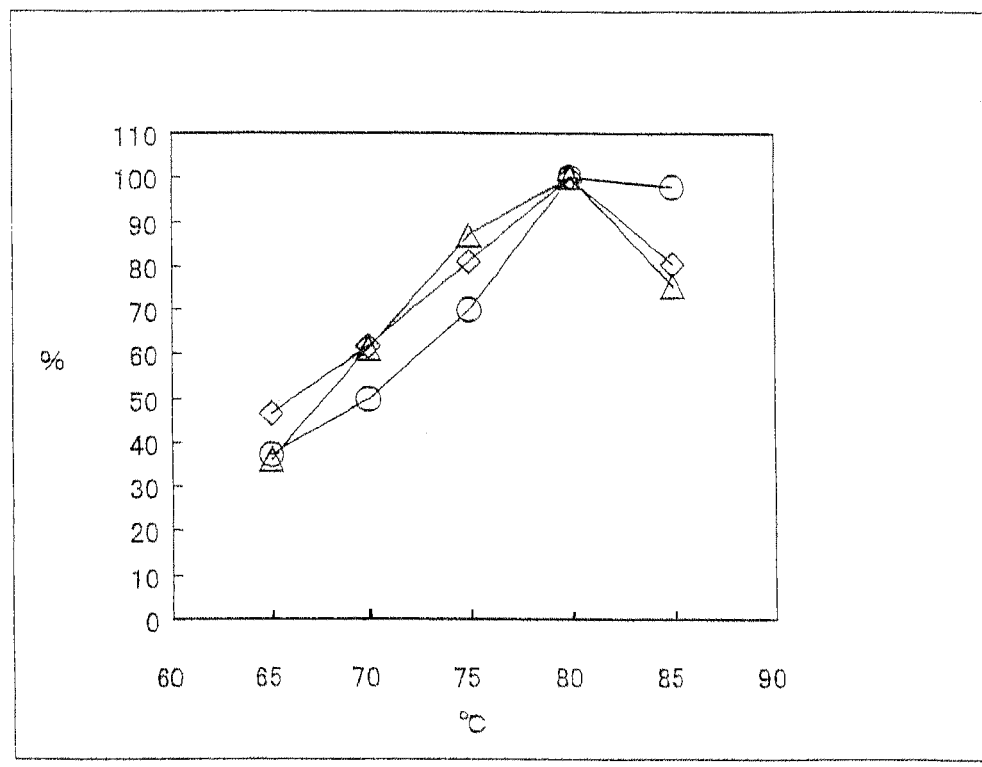
FIG. 1 illustrates the relationship between the DNA polymerase activity and the reaction temperature. In the figure, ◇, Δ and ○ represent results for Tks DNA polymerase, Tce DNA polymerase and Tsi DNA polymerase, respectively.

As used herein, a polypeptide having a DNA polymerase activity refers to a polypeptide that incorporates four kinds of deoxyribonucleoside triphosphates (dATP, dGTP, dCTP and dTTP) according to a nucleotide sequence of a template DNA and catalyzes polymerization of a DNA strand complementary to the template DNA.

As used herein, suitability for primer extension refers to excellence in the ability to synthesize a DNA from a primer using, as a substrate, a complex in which a primer is annealed to a single-stranded template DNA. It is exemplified by a high affinity for a single-stranded DNA. It is expected that a DNA polymerase having a high affinity for a single-stranded DNA results in high sensitivity in a nucleic acid amplification reaction. Thus, it is useful for a reaction of amplifying a nucleic acid from a template nucleic acid present at low copy number. An exemplary index of affinity of a DNA polymerase for a single-stranded DNA is a Km value for M13 phage single-stranded DNA. The Km value is preferably 2.5 μg/ml or less, more preferably 2.0 μg/ml or less, still more preferably 1.5 μg/ml or less.

As used herein, high fidelity refers to highly accurate nucleotide incorporation upon a DNA synthesis reaction with a DNA polymerase. Examples of determination methods thereof include the Kunkel method (J. Biol. Chem. 1985 May 10; 260(9):5787-96), the sequencing method, and the method of Cline et al. (Nucleic Acids Res. 1996 Sep. 15; 24(18):3546-51). Among these, the sequencing method is the most reliable. Although it is not intended to limit the present invention, for example, it is possible to estimate the fidelity as follows: PCR is carried out using a genomic DNA from *Thermus thermophilus* HB-8 as a template and a DNA polymerase; the amplification products are cloned into a vector pUC118; the about 500-bp nucleotide sequences of the amplified fragments in plural clones are determined; the number of nucleotides considered to be erroneous is determined; and the percentage of erroneous nucleotides in total sequenced nucleotides is determined.

Hereinafter, the present invention will be described in detail.

(1) The Polypeptide Having a DNA Polymerase Activity of the Present Invention and a Gene Encoding the Polypeptide The polypeptide having a DNA polymerase activity of the present invention is a polypeptide that is more suitable for primer extension than the Pfu-derived DNA polymerase and the KOD-derived DNA polymerase, and is excellent in accuracy upon DNA synthesis. The polypeptide having a DNA polymerase activity of the present invention is more excellent than Pyrobest DNA polymerase (Takara Bio) (from a representative high-fidelity thermostable DNA polymerase, the Pfu-derived DNA polymerase), and KOD DNA polymerase, KOD dash DNA polymerase and KOD plus DNA polymerase (all from Toyobo) in the DNA chain length that can be amplified using the PCR method and the fidelity of the reaction.

The physical and chemical properties of the DNA polymerase of the present invention are as follows:
(i) Molecular weight: about 85-90 kilodalton as determine by the SDS-PAGE method
(ii) Optimal temperature: 75-85° C.
(iii) Optimal pH: 5.5-6.5 (75° C.)

There is no specific limitation concerning the polypeptide having a DNA polymerase activity of the present invention as long as it has the above-mentioned physical and chemical properties. For example, it can be obtained from *Thermococcus* sp. KS-1 (hereinafter referred to as Tks), *Thermococcus siculi* (hereinafter referred to as Tsi) and *Thermococcus celer* (hereinafter referred to as Tce).

The polypeptide having a DNA polymerase activity of the present invention may consist of an amino acid sequence of SEQ ID NO:16, 24 or 32, or it may be a functional equivalent having an activity substantially equivalent thereto. A mutation such as deletion, insertion, addition or substitution of an amino acid in an amino acid sequence may be generated in a naturally occurring polypeptide. Such a mutation may be generated due to a polymorphism or a mutation of the gene encoding the polypeptide, or due to a modification reaction of the polypeptide in vivo or during purification after synthesis. It is known that such a mutated polypeptide may nevertheless exhibit a physiological or biological activity substantially equivalent to that of a polypeptide without a mutation. The present invention also encompasses such a functional equivalent for which no significant difference in the function or activity is recognized in spite of the difference in the structure. There is no specific limitation concerning the number of mutated amino acids as long as the polypeptide exhibits a substantially equivalent physiological or biological activity. It is exemplified by a mutation (deletion, insertion, addition, substitution, etc.) of 1 or more, for example 1 to several, more specifically 1 to 10 amino acids. This is applicable to one in which such a mutation is artificially introduced into an amino acid sequence of a polypeptide. In this case, it is possible to make further various mutants.

When a polypeptide is to be produced using genetic engineering techniques, it is often expressed as a fusion polypeptide. For example, an N-terminal peptide chain derived from another polypeptide may be added at the N terminus of the polypeptide of interest in order to increase the expression level of the polypeptide. In another case, an appropriate peptide chain (e.g., histidine tag, glutathione-S-transferase) may be added at the N terminus or the C terminus of the polypeptide of interest, and the polypeptide is then expressed. Thereby, the purification of the polypeptide of interest is facilitated by using a carrier having an affinity for the peptide chain. A DNA polymerase having an amino acid sequence partially different from the DNA polymerase of the present invention may be within the scope of the present invention as "a functional equivalent" provided that it exhibits an activity essentially equivalent to the DNA polymerase of the present invention.

DNAs encoding the polypeptide having a DNA polymerase activity of the present invention include a DNA containing a nucleotide sequence encoding the amino acid sequence of SEQ ID NO:16, 24 or 32, or a part thereof (e.g., a DNA containing the nucleotide sequence of SEQ ID NO:15, 23 or 31, or a part thereof). A DNA encoding a polypeptide having the function as a DNA polymerase that consists of an amino acid sequence in which 1 or more, for example 1 to several, more specifically 1 to 10 amino acids are deleted, inserted, added or substituted in the amino acid sequence of SEQ ID NO:16, 24 or 32 is also included. Also, a nucleotide sequence encoding a polypeptide having the function as a DNA polymerase that is capable of hybridizing to a DNA consisting of a nucleotide sequence complementary to such a DNA under stringent conditions is within the scope of the present invention. For example, "stringent conditions" refer to the conditions under which incubation with a probe is carried out in 6×SSC (1×SSC: 0.15 M NaCl, 0.015 M sodium citrate, pH 7.0) containing 0.5% SDS, 5×Denhardt's and 100 µg/ml of denatured salmon sperm DNA at 68° C. for 12 to 20 hours. For example, a DNA hybridized to a probe can be detected after washing in 0.1×SSC containing 0.5% SDS at 68° C.

The gene of the present invention may contain a sequence encoding a region called intein which is spontaneously excised from a polypeptide after translation into the polypeptide. A DNA containing such a sequence is also encompassed by the present invention as long as it encodes a polypeptide having a DNA polymerase activity.

Although it is not intended to limit the present invention, for example, "a polypeptide having a DNA polymerase activity" is preferably a polypeptide having a DNA polymerase activity that exhibits the above-mentioned various physical and chemical properties.

The expression "a DNA containing a nucleotide sequence encoding an amino acid sequence" as used herein is explained below. It is known that one to six codon(s) (a combination of three bases), which defines an amino acid in a gene, is assigned for each amino acid. Thus, many DNAs can encode one specific amino acid sequence although it depends on the amino acid sequence.

Furthermore, it is not difficult to artificially produce various genes encoding the same amino acid sequence if one uses various genetic engineering techniques. For example, if a codon used in an original gene encoding a polypeptide of interest is one whose codon usage is low in the host to be used for producing the polypeptide using genetic engineering techniques, the expression level of the polypeptide may be low. In this case, the codon is artificially converted into one frequently used in the host without altering the encoded amino acid sequence aiming at elevating the expression level of the polypeptide of interest (e.g., JP-B 7-102146). As described above, various genes encoding one specific amino acid sequence can be artificially produced, of course, and may be generated in nature. Thus, a gene that does not have a nucleotide sequence identical to the nucleotide sequence disclosed herein may be encompassed by the present invention provided that it encodes the amino acid sequence disclosed herein.

The polypeptide having a DNA polymerase activity of the present invention is suitable for in vitro primer extension. For example, when a DNA polymerase activity is measured using a substrate in which a primer is annealed to a single-stranded DNA (a substrate in which HT Primer (SEQ ID NO:33) is annealed to M13 single-stranded DNA; hereinafter also referred to as M13/HT Primer substrate or primer extension-type substrate), a nucleotide incorporation activity higher than that observed using an activated DNA (DNase I-treated calf thymus DNA) which is usually used for activity measurement is observed.

The value of a ratio of a DNA polymerase activity measured using the M13/HT Prime substrate (hereinafter also referred to as an extension activity) to a DNA polymerase activity measured using the activated DNA as a substrate (hereinafter also referred to as an incorporation activity) (extension activity/incorporation activity) for the polypeptide having a DNA polymerase activity of the present invention is higher than that for a known DNA polymerase derived from *Pyrococcus furiosus* (Pfu DNA polymerase; Stratagene), Taq DNA polymerase derived from *Thermus aquaticus* (TaKaRa Taq, Takara Bio) or KOD DNA polymerase derived from *Thermococcus kodakaraensis* (KOD DNA polymerase, Toyobo).

When the activated DNA as a competitive substrate is added to a reaction system using the M13/HT Primer substrate, the primer extension activities of the above-mentioned three DNA polymerases are strongly inhibited. On the other hand, the polypeptide having a DNA polymerase activity of the present invention is inhibited only slightly, demonstrating that this polypeptide has a high affinity for the primer extension-type substrate.

The fact that the Km value for M13 phage single-stranded DNA of the polypeptide having a DNA polymerase activity of the present invention is 2 µg/ml or less also shows that this polypeptide has a high affinity for the primer extension-type substrate.

(2) The Method for Producing a Polypeptide Having a DNA Polymerase Activity of the Present Invention For example, it is possible to produce the polypeptide having a DNA polymerase activity of the present invention in large quantities from a culture of a Tks, Tsi or Tce strain, or from a transformant into which a gene encoding the polypeptide is transferred.

A DNA encoding the polypeptide of the present invention can be obtained using a genomic DNA from a microorganism producing the polypeptide of the present invention as a starting material. There is no specific limitation concerning the method for preparing the genomic DNA. In an exemplary method, an archaebacterium of the genus *Thermococcus* is anaerobically cultured at 85° C., the grown cells are disrupted, and a DNA is extracted and purified. Known methods can be used for various procedures used for gene cloning such as a method for cleaving the thus obtained DNA with a restriction enzyme. Such methods are described in detail in J. Sambrook et al., Molecular Cloning, A Laboratory Manual, 3rd ed., 2001, Cold Spring Harbor Laboratory.

The polypeptide having a DNA polymerase activity of the present invention can be expressed in cells by culturing a transformant transformed with a recombinant plasmid into which a nucleic acid encoding a polypeptide having a DNA polymerase activity (for example, without limitation, a nucleic acid having the nucleotide sequence of SEQ ID NO:15, 23 or 31) or a part thereof is incorporated under appropriate culture conditions (for example, in case of an *Escherichia coli* host, in LB medium (10 g/l Tryptone, 5 g/l yeast extract, 5 g/l NaCl, pH 7.2)). The polypeptide can be obtained from the cultured cells by conducting, for example, sonication, heating, and chromatography using cation exchange column, affinity carrier column, gel filtration column, anion exchange column or the like.

The molecular weight of the thus obtained polypeptide having a DNA polymerase activity of the present invention as determined by SDS-PAGE is about 85-90 dalton.

The optimal pH of the polypeptide having a DNA polymerase activity of the present invention exhibited in a Tris buffer at 75° C. is pH 5.5 to 6.5. When the enzymatic activity of the DNA polymerase is measured at various temperatures, it exhibits a high activity at 75 to 85° C. The polypeptide having a DNA polymerase activity of the present invention is highly thermostable.

The polypeptide having a DNA polymerase activity of the present invention is accompanied by a 3'>5' exonuclease activity. The degree of the exonuclease activity relative to the DNA polymerase activity exceeds the activity ratio of Pfu DNA polymerase, which is known to result in very high accuracy upon DNA synthesis due to its high exonuclease activity. The frequency of errors occurring during a DNA synthesis reaction measured for the polypeptide having a DNA polymerase activity of the present invention is lower than that of the Pfu-derived DNA polymerase. The above-mentioned various properties show that the DNA polymerase of the present invention is very excellent as a reagent for genetic engineering (e.g., for the PCR method).

(3) The Method for Amplifying a Nucleic Acid Using the DNA Polymerase of the Present Invention, as Well as the Composition and the Kit for the Method The polypeptide having a DNA polymerase activity of the present invention is characterized in that it results in high fidelity and is suitable for primer extension. Thus, a method for accurately amplifying, analyzing or identifying a target nucleic acid, as well as a composition and a kit for the method are provided using the polypeptide.

The polypeptide having a DNA polymerase activity of the present invention exhibits very excellent performance upon use in the PCR method due to the above-mentioned characteristics. For example, it is difficult to amplify a DNA fragment of 6 kilobase pairs or more using a DNA polymerase derived from *Thermococcus kodakaraensis* (NOD DNA polymerase, Toyobo) which is utilized for the PCR method, alone. A DNA fragment of 15 kilobase pairs or more can be amplified only if it is used in combination with another DNA polymerase. On the other hand, it is possible to amplify a DNA fragment of 15 kilobase pairs using the DNA polymerase of the present invention alone without adding another enzyme.

The composition or the kit containing the polypeptide of the present invention is superior to a conventional DNA polymerase or composition containing plural DNA polymerases (for example, a composition or a kit containing KOD DNA polymerase; a composition or a kit containing KOD dash DNA polymerase; or a composition or a kit containing KOD plus DNA polymerase) in that it can be used to accurately amplify, analyze or identify a target nucleic acid.

The above-mentioned composition or kit is exemplified by one containing the polypeptide having a DNA polymerase activity of the present invention, a buffer optimized for the polypeptide, four kinds of dNTPs and a divalent cation. It may further contain a set of primers for amplifying and/or detecting a target nucleic acid.

The present invention provides an antibody that binds to the polypeptide of the present invention. There is no specific limitation concerning the antibody as long as it is capable of recognizing and specifically binding to the polypeptide of the present invention. It may be either a polyclonal antibody or a monoclonal antibody. Furthermore, an antibody fragment (e.g., a Fab fragment), a single-chain antibody or the like having the same recognition characteristic as the above-mentioned antibody is also encompassed by the present invention.

The antibody of the present invention can be prepared by immunizing a mouse or a rabbit with the polypeptide of the present invention or a portion thereof as an antigen according to a known method such as the method as described in Current Protocols in Immunology, 1992, John Wiley & Sons, Inc. Furthermore, a monoclonal antibody can be produced by generating a hybridoma from antibody-producer cells collected from the immunized animal according to a conventional method.

The antibody can be used for detection or purification of the polypeptide of the present invention. In addition, it can be used to inhibit an activity of the polypeptide such as a DNA polymerase activity or a 3'>5' exonuclease activity. For example, an antibody capable of suppressing a DNA polymerase activity is useful in PCR for suppressing DNA extension from a nonspecifically annealed primer at a low temperature before initiation of a reaction. Furthermore, an antibody capable of suppressing a 3'>5' exonuclease activity is useful in PCR for suppressing degradation of primers prior to initiation of a reaction, for example.

EXAMPLES

The following Examples illustrate the present invention in more detail, but are not to be construed to limit the scope thereof.

Example 1

An activated DNA used for measuring an activity of a DNA polymerase in Examples was prepared as follows.

Briefly, salmon sperm DNA (Sigma) or calf thymus DNA (Worthington) was activated by treatment with DNase I. This method was based on the method as described by C. C. Richardson in D. R. Davis (ed.), "DNA polymerase from *Escherichia coli*", pp. 263-276, Harper & Row.

An activity of a DNA polymerase was measured as follows.

Briefly, a sample to be subjected to activity measurement was reacted in 50 μl of a reaction mixture for activity measurement (20 mM Tris-hydrochloride buffer (pH 8.3), 10 mM potassium chloride, 6 mM ammonium sulfate, 2 mM magnesium chloride, 0.1% Triton X-100, 0.001% bovine serum albumin, 200 μM each of dATP, dGTP and dCTP, 100 μM dTTP, 0.238 μM [$^3$H]-Methyl TTP, 0.4 mg/ml activated salmon sperm DNA) at 74° C. for 5 minutes.

After reaction, 500 μl of 20% trichloroacetic acid (TCA) containing 2% Nappi (Nacalai Tesque) and 500 μl of sheared DNA were added thereto. After allowing to stand on ice for 15 minutes or longer, the mixture was subjected to collection on a glass filter (Whatman). The glass filter was washed seven times with 5 ml of 5% TCA containing 2% Nappi followed by ethanol and dried, and the radioactivity was measured using a liquid scintillation counter. An activity of an enzyme that incorporates 10 nmol of total nucleotide into an acid-insoluble precipitate in 30 minutes according to the above-mentioned enzymatic activity measurement method was defined as 1 U.

Example 2

Genomic DNAs were prepared from *Thermococcus* sp. KS-1 (JCM11816), *Thermococcus celer* (JCM8558) and *Thermococcus siculi* (DSMZ12349) according to the following method.

Briefly, 10 ml of a purchased culture was centrifuged at 8,000 rpm for 10 minutes. The resulting supernatant and a dark layer at the interface between the supernatant and the precipitate were further centrifuged at 15,000 rpm for 10 minutes. The resulting precipitate was suspended in 0.8 ml of 20% sucrose in 50 mM Tris-hydrochloride buffer (pH 8.0). 0.16 ml of 500 mM EDTA (pH 8.0) and 0.08 ml of 10 mg/ml lysozyme chloride (Nacalai Tesque) aqueous solution were added thereto. The mixture was reacted at room temperature for 2 hours.

After reaction, 6.4 ml of a solution containing 150 mM NaCl, 1 mM EDTA and 20 mM Tris-HCl buffer (pH 8.0), 0.08 ml of 20 mg/ml proteinase K (Takara Bio) and 0.4 ml of 10% sodium lauryl sulfate aqueous solution were added to the reaction mixture. The resulting mixture was incubated at 37° C. for 1 hour. An equal volume of a mixture of phenol saturated with 100 mM Tris-hydrochloride buffer (pH 8.0)/chloroform/isoamyl alcohol (25:24:1, v/v) was then added thereto. The mixture was gently mixed for 10 minutes, and then centrifuged at 10,000×g for 10 minutes twice. After centrifugation, the thus obtained supernatant was subjected to ethanol precipitation, and the precipitate was dissolved in 0.1 ml of TE buffer to obtain a genomic DNA solution.

Example 3

(1) Cloning of Middle Portion of DNA Polymerase Gene

Oligonucleotides TPPolBF4, TPPolBF5, TTPolBR1 and TTPolBR4 (SEQ ID NOS:1-4) were synthesized using a DNA synthesizer on the basis of portions conserved among amino acid sequences of various thermostable DNA polymerases.

A PCR was carried out in a volume of 100 μl using 250 ng of the *Thermococcus* sp. KS-1 genomic DNA prepared in Example 2 as a template, as well as a combination of primers (50 pmol each) TPPolBF4 and TTPolBR1, TPPolBF4 and TTPolBR4, or TPPolBF5 and TTPolBR1. TaKaRa Ex Taq (Takara Bio) was used as a DNA polymerase for the PCR according to the attached protocol. The PCR reaction was carried out as follows: 94° C. for 3 minutes; and 40 cycles of 94° C. for 30 seconds, 50° C. for 30 seconds and 72° C. for 2 minutes.

After reaction, the reaction mixtures were treated with phenol and subjected to Microcon-100 (Takara Bio) for removal of primers and concentration of the amplified DNA fragments.

The nucleotide sequences of the concentrated amplified fragments TPPolBF4-TTPolBR1 (3 kb), TPPolBF4-TTPolBR4 (2 kb) and TPPolBF5-TTPolBR1 (0.7 kb) were determined by direct sequencing, and compared with amino acid sequences of various thermostable DNA polymerases. As a result, it was shown that *Thermococcus* sp. KS-1 DNA polymerase contains an intein sequence.

(2) Cloning of Upstream Portion of DNA Polymerase Gene

A specific oligonucleotide Tks01 (SEQ ID NO:5) for cloning the upstream portion was synthesized on the basis of the nucleotide sequence determined in Example 3-(1). In addition, 32 primers as shown in Table 1 were synthesized. The tag sequence in Table 1 is shown in SEQ ID NO:6.

TABLE 1

5'-tag sequence -NN-SSSSSSS-3'
(N: mixture of G, A, T and C; S represents the nucleotide sequence below.)

| No. | Nucleotide sequence | No. | Nucleotide sequence | No. | Nucleotide sequence |
|---|---|---|---|---|---|
| 1 | gcccaaa | 13 | gccgtat | 25 | gtggaca |
| 2 | gctcata | 14 | gggattt | 26 | gtcccaa |
| 3 | gtggcga | 15 | gtcaagc | 27 | gctgcta |
| 4 | gaaagcc | 16 | gcgttat | 28 | ggcgggc |
| 5 | gaggtag | 17 | gggcaag | 29 | gccgtcg |
| 6 | gcttttg | 18 | gatcatc | 30 | gaaccgt |
| 7 | gtatccg | 19 | gtagcgg | 31 | gttccac |
| 8 | ggacggt | 20 | gcgtgct | 32 | ggtgcag |
| 9 | gcaaaac | 21 | gcgttca | | |

TABLE 1-continued

5'-tag sequence -NN-SSSSSSS-3'
(N: mixture of G, A, T and C; S represents the nucleotide sequence below.)

| No. | Nucleotide sequence | No. | Nucleotide sequence | No. | Nucleotide sequence |
|---|---|---|---|---|---|
| 10 | gatcatc | 22 | gggcgaa | | |
| 11 | gtgccgc | 23 | gtcttca | | |
| 12 | gcgggcg | 24 | gggtaaa | | |

PCRs were carried out in 50-41 reaction mixtures each containing 1 ng of the *Thermococcus* sp. KS-1 genomic DNA prepared in Example 2 as a template, a combination of 10 pmol of Tks01 and 10 pmol of one of the 32 primers listed in Table 1, 20 mM Tris-acetate buffer (pH 8.5), 50 mM potassium acetate, 3 mM magnesium acetate, 0.01% BSA, 300 μM each of dNTPs and 1.25 U of TaKaRa Ex Taq DNA polymerase (Takara Bio). PCRs were carried out as follows: incubation at 94° C. for 3 minutes; and 40 cycles of 98° C. for 10 seconds, 50° C. for 10 seconds and 72° C. for 40 seconds. A portion of each PCR product was subjected to agarose gel electrophoresis. Microcon-100 (Takara Bio) was used to remove primers from the reaction mixtures selected for the generation of single bands and to concentrate the reaction mixtures. The concentrates were subjected to direct sequencing to screen for fragments containing the upstream portion of the DNA polymerase. As a result, it was shown that an about 1300-bp PCR-amplified fragment Tks012G contained the upstream portion of the DNA polymerase gene of interest. Furthermore, it was confirmed that this fragment contained an intein sequence different from that in Example 3-(1).

A specific oligonucleotide Tks04 (SEQ ID NO:7) for cloning the further upstream portion around the start codon was synthesized on the basis of the sequence of Tks012G. PCRs were carried out in the 50-μl reaction mixtures using 1 ng of the *Thermococcus* sp. KS-1 genomic DNA prepared in Example 2 as a template, as well as a combination of 10 pmol of Tks04 and 10 pmol of one of the 32 primers listed in Table 1. The conditions for PCRs and the purification procedure were as described above. The amplified fragments were subjected to direct sequencing to screen for fragments containing the upstream portion of the DNA polymerase. As a result, it was shown that an about 1800-bp PCR-amplified fragment Tks041B contained the portion around the start codon of the DNA polymerase gene of interest.

(3) Cloning of Downstream Portion of DNA Polymerase Gene

A specific oligonucleotide Tks02 (SEQ ID NO:8) for cloning the upstream portion was synthesized on the basis of the nucleotide sequence determined in Example 3-(1). PCRs were carried out using 1 ng of the *Thermococcus* sp. KS-1 genomic DNA prepared in Example 2 as a template, as well as a combination of 10 pmol of Tks02 and 10 pmol of one of the 32 primers listed in Table 1. The conditions for PCRs were as described above. A portion of each PCR product was subjected to agarose gel electrophoresis. An about 2500-bp DNA fragment of Tks022D was recovered, blunted with T4 DNA polymerase (Takara Bio) and ligated using T4 DNA ligase (Takara Bio) to pUC118 (Takara Bio) which had been digested with HincII (Takara Bio). The plasmid was used to transform *Escherichia coli* JM109. The transformant was cultured to obtain a plasmid pTks022D having the inserted about 2500-bp DNA fragment, and the nucleotide sequence of the inserted DNA fragment was determined.

(4) Construction of Plasmid for Expressing DNA Polymerase

It was shown that two intein sequences are contained in the sequence of *Thermococcus* sp. KS-1 DNA polymerase.

Then, a DNA polymerase gene from which the intein sequences were eliminated was constructed.

Oligonucleotides TksNde, Tks1EndBg, Tks2StaBg, Tks2EndBal, Tks3StaBal and TksBgPs (SEQ ID NOS:9-14) were synthesized on the basis of the sequence determined in Example 3-(3).

PCRs were carried out in volumes of 100 μl using 100 ng of the *Thermococcus* sp. KS-1 genomic DNA prepared in Example 2 as a template, as well as a combination of primers (20 pmol each) TksNde and Tks1EndBg (TksA), Tks2StaBg and Tks2EndBal (TksB) or Tks3StaBal and TksBgPs (TksC). Pyrobest (Takara Bio) was used as a DNA polymerase for the PCR according to the attached protocol. The reaction was carried out as follows: 40 cycles of 94° C. for 30 seconds, 50° C. for 30 seconds and 72° C. for 3 minutes. Then, the following amplified DNA fragments were obtained: about 1.3-kb TksA; about 0.3-kb TksB; and about 0.9-kb TksC. In addition, a PCR was carried out in a similar manner under the above-mentioned conditions in a volume of 100 μl using a mixture of 1 μl of the PCR reaction mixture TksB and 1 μl of the PCR reaction mixture TksC as a template, as well as 20 pmol of Tks2StaBg and 20 pmol of TksBgPs (TksD) as primers. Then, an about 1.2-kb amplified DNA fragment TksD was obtained.

The DNA fragment TksA was digested with restriction enzymes NdeI and BglII. The DNA fragment TksD was digested with restriction enzymes BglII and PstI. They were ligated to pTV119Nd (a plasmid in which the NcoI site in pTV119N is converted into a NdeI site) which had been digested with restriction enzymes NdeI and PstI according to a conventional method to construct a plasmid pTks59. This plasmid is designated and indicated as pTks59, and deposited on May 14, 2004 (date of original deposit) at International Patent Organism Depositary, National Institute of Advanced Industrial Science and Technology, AIST Tsukuba Central 6, 1-1, Higashi 1-Chome, Tsukuba-shi, Ibaraki-ken 305-8566, Japan under accession number FERM BP-10312.

(5) Determination of Nucleotide Sequence of DNA Fragment Containing DNA Polymerase Gene The nucleotide sequence of the DNA fragment inserted into pTks59 obtained in Example 3-(4) was determined according to a dideoxy method.

Analysis of the determined nucleotide sequence revealed the existence of an open reading frame presumably encoding a DNA polymerase of interest. The nucleotide sequence of the open reading frame is shown in SEQ ID NO:15. The amino acid sequence of DNA polymerase deduced from the nucleotide sequence is shown in SEQ ID NO:16.

(6) Expression of *Thermococcus* sp. KS-1 DNA Polymerase Gene

*Escherichia coli* JM109 transformed with pTks59 was inoculated into 5 ml of LB medium (1% Tryptone, 0.5% yeast extract, 0.5% sodium chloride) containing 100 μg/ml of ampicillin and cultured at 37° C. for 6 hours. 50 μl of the culture was inoculated into 5 ml of LB medium containing 100 μg/ml of ampicillin and 1 mM IPTG, and cultured with shaking at 37° C. overnight. After cultivation, cells collected by centrifugation were suspended in 36 μl of sonication buffer (50 mM Tris-hydrochloride (pH 8.0), 2 mM 2-mercaptoethanol, 10% glycerol) and sonicated. A supernatant obtained by centrifuging the sonicated suspension at 12,000 rpm for 10 minutes was heated at 80° C. for 10 minutes and then centrifuged again at 12,000 rpm for 10 minutes to collect a supernatant as a heated supernatant.

The enzymatic activity of the heated supernatant was measured according to the method as described in Example 1. As a result, a DNA polymerase activity was observed.

(7) Preparation of Purified DNA Polymerase Preparation

*Escherichia coli* JM109 transformed with the plasmid pTks59 obtained in Example 3-(5) was inoculated into 400 ml of LB medium containing 50 μg/ml of ampicillin and 0.1% glucose, and cultured with shaking at 37° C. overnight. The whole culture was added to 20 liters of LB medium containing 50 μg/ml of ampicillin and cultured at 37° C. to OD660 of 1.0. When OD600 reached 1.0, IPTG was added at a final concentration of 0.2 mM, and the cultivation was continued at 37° C. for 4 hours. After cultivation, cells collected by centrifugation were suspended in 732 ml of Buffer A (50 mM Tris-hydrochloride buffer (pH 7.5), 2 mM EDTA, 2 mM dithiothreitol, 1 mM phenylmethanesulfonyl fluoride) and sonicated. The sonicated suspension was centrifuged at 12,000 rpm for 30 minutes. Ammonium sulfate was added to the resulting supernatant at a final concentration of 0.2 M. The mixture was heated at 75° C. for 15 minutes and allowed to stand at 0° C. for 30 minutes. It was centrifuged again at 12,000 rpm for 30 minutes. The supernatant was subjected to nucleic acid removal using polyethyleneimine and ammonium sulfate precipitation, and dialyzed against 2 liters of Buffer B (50 mM Tris-hydrochloride buffer (pH 7.5), 1 mM EDTA, 10% glycerol, 1 mM dithiothreitol, 1 mM phenylmethanesulfonyl fluoride) twice for 2 hours and once overnight. After dialysis, 200 ml of the enzyme solution was subjected to Phosphocellulose P-11 column (Whatman) equilibrated with Buffer B. Elution was carried out with a linear gradient of 0 to 500 mM potassium phosphate buffer (pH 7.5) using FPLC system (Amersham Pharmacia Biotech).

The eluted DNA polymerase fraction was dialyzed against 1 liter of Buffer C (20 mM Tris-hydrochloride buffer (pH 7.5), 0.1 mM EDTA, 10% glycerol, 0.2% Tween 20, 1 mM dithiothreitol) twice for 2 hours and once overnight. After dialysis, 100 ml of the enzyme solution was subjected to Heparin-Sepharose CL-6B (Pharmacia Pharmacia Biotech) equilibrated with Buffer B. Elution was carried out with a linear gradient of 0 to 700 mM KCl using FPLC system.

The fraction was dialyzed against 1 liter of Buffer D (20 mM Tris-HCl (pH 9.0), 0.1 mM EDTA, 10% glycerol, 0.2% Tween 20, 1 mM dithiothreitol) twice for 2 hours and once overnight. After dialysis, 50 ml of the enzyme solution was subjected to Q-Sepharose (Pharmacia Pharmacia Biotech) equilibrated with Buffer D. Elution was carried out with a linear gradient of 0 to 300 mM NaCl using FPLC system.

The fraction was dialyzed against 1 liter of storage buffer (50 mM Tris-HCl (pH 8.2), 0.1 mM EDTA, 10 mM sodium chloride, 0.1% Tween 20, 0.1% Nonidet P-40, 1 mM dithiothreitol, 50% glycerol) twice for 2 hours and once overnight. The thus obtained DNA polymerase was used as Tks DNA polymerase preparation.

The activity of the Tks DNA polymerase preparation was measured according to the method as described in Example 1. As a result, a DNA polymerase activity was observed.

Example 4

(1) Cloning of Middle Portion of DNA Polymerase Gene

Oligonucleotides TPPolBF1, TPPolBF5, TTPolBR1 and TTPolBR5 (SEQ ID NOS:17 2, 3, 18) were synthesized on the basis of portions conserved among amino acid sequences of various thermostable DNA polymerases.

A PCR was carried out in a volume of 100 μl using 250 ng of the *Thermococcus celer* genomic DNA prepared in Example 2 as a template, as well as a combination of primers (50 pmol each) TPPolBF1 and TTPolBR1, TPPolBF1 and TTPolBR5, or TPPolBF5 and TTPolBR1. The conditions for PCRs and the purification procedure were as described in Example 3-(1). The nucleotide sequences of the amplified fragments TPPolBF1-TTPolBR1 (about 2 kb), TPPolBF1-TTPolBR5 (about 1 kb) and TPPolBF5-TTPolBR1 (about 0.8 kb) were determined by direct sequencing.

(2) Cloning of Upstream and Downstream Portions of DNA Polymerase Gene

Specific oligonucleotides Tce01 (SEQ ID NO:19) for cloning the upstream portion and Tce02 (SEQ ID NO:20) for cloning the downstream portion were synthesized on the basis of the nucleotide sequence determined in Example 4-(1).

PCRs were carried out using 1 ng of the *Thermococcus celer* genomic DNA prepared in Example 2 as a template, as well as a combination of 10 pmol of Tce01 or Tce02 and 10 pmol of one of the 32 primers listed in Table in Example 3-(2). The conditions for PCRs and the 25" purification procedure were as described in Example 3-(2). The amplification products were subjected to direct sequencing to screen for fragments containing the upstream region of the DNA polymerase of interest. As a result, it was shown that an about 650-bp PCR-amplified fragment Tce013C contained the upstream portion of the DNA polymerase gene, and an about 650-bp PCR-amplified fragment Tce022F contained the downstream portion of the DNA polymerase gene.

(3) Construction of Plasmid for Expressing DNA Polymerase

Oligonucleotides TceNde and TceBgPs (SEQ ID NOS:21 and 22) were synthesized on the basis of the sequence determined in Example 4-(2).

PCRs were carried out in volumes of 100 μl using 100 ng of the *Thermococcus celer* genomic DNA prepared in Example 2 as a template, as well as a combination of primers (20 pmol each) TceNde and TceBgPs. Pyrobest (Takara Bio) was used as a DNA polymerase for the PCR according to the attached protocol. The reaction was carried out as follows: 40 cycles of 94° C. for 30 seconds, 50° C. for 30 seconds and 72° C. for 2 minutes. The about 2.3-kb amplified DNA fragment was digested with restriction enzymes NdeI and BglII (both from Takara Bio). The DNA fragment was integrated between NdeI and BamHI sites in a plasmid vector pTV119Nd (a plasmid in which the NcoI site in pTV119N is converted into a NdeI site) to construct a plasmid pTce19. This plasmid is designated and indicated as pTce19, and deposited on May 14, 2004 (date of original deposit) at International Patent Organism Depositary, National Institute of Advanced Industrial Science and Technology, AIST Tsukuba Central 6, 1-1, Higashi 1-Chome, Tsukuba-shi, Ibaraki-ken 305-8566, Japan under accession number FERM BP-10311.

(4) Determination of Nucleotide Sequence of DNA Fragment Containing DNA Polymerase Gene The nucleotide sequences of the DNA fragment inserted into pTce19 was determined according to a dideoxy method.
Analysis of the determined nucleotide sequence revealed the existence of an open reading frame presumably encoding a DNA polymerase of interest. The nucleotide sequence of the open reading frame is shown in SEQ ID NO:23. The amino acid sequence of DNA polymerase deduced from the nucleotide sequence is shown in SEQ ID NO:24.

(5) Expression of *Thermococcus Celer* DNA Polymerase Gene

*Escherichia coli* JM109 transformed with pTce19 was cultured according to the method as described in Example 3-(6). Cells collected by centrifugation were suspended in 64 µl of sonication buffer and sonicated. A supernatant obtained by centrifuging the sonicated suspension at 12,000 rpm for 10 minutes was heated at 80° C. for 10 minutes and then centrifuged again at 12,000 rpm for 10 minutes to collect a supernatant as a heated supernatant.
The enzymatic activity of the heated supernatant was measured according to the method as described in Example 1. As a result, a DNA polymerase activity was observed.

(6) Preparation of Purified DNA Polymerase Preparation

*Escherichia coli* JM109 transformed with pTce19 was cultured according to the method as described in Example 3-(7). Purification was carried out following the procedure as described in Example 3-(7) to the step of elution from Heparin-Sepharose CL-6B (Pharmacia Biotech) with a linear gradient of 0 to 700 mM KCl.
The eluted DNA polymerase fraction was dialyzed against 1 liter of Buffer C containing 0.3 M sodium chloride twice for 2 hours and once overnight. After dialysis, 95 ml of the enzyme solution was subjected to Superdex G200 (Pharmacia Biotech) equilibrated with Buffer C containing 0.3 M sodium chloride. Elution was carried out with Buffer C containing 0.3 M sodium chloride.
The eluted DNA polymerase fraction was dialyzed against 1 liter of Buffer D twice for 2 hours and once overnight. After dialysis, 45 ml of the enzyme solution was subjected to Q-Sepharose (Pharmacia Pharmacia Biotech) equilibrated with Buffer D. Elution was carried out with a linear gradient of 0 to 300 mM NaCl using FPLC system.
The fraction was dialyzed against 1 liter of storage buffer twice for 2 hours and once overnight. The thus obtained DNA polymerase was used as Tce DNA polymerase preparation.
The enzymatic activity of the Tce DNA polymerase preparation was measured according to the method as described in Example 1. As a result, a DNA polymerase activity was observed for the Tce DNA polymerase preparation.

Example 5

(1) Cloning of Middle Portion of DNA Polymerase Gene

Oligonucleotides TPPolBF1, TPPolBF5, TTPolBR1, TTPolBR4 and TTPolBR5 (SEQ ID NOS:17, 2, 3, 4, 18) were synthesized on the basis of portions conserved among amino acid sequences of various thermostable DNA polymerases.
A PCR was carried out in a volume of 100 µl using 250 ng of the *Thermococcus siculi* genomic DNA prepared in Example 2 as a template, as well as a combination of primers (50 pmol each) TPPolBF1 and TTPolBR4, TPPolBF1 and TTPolBR5, or TPPolBF5 and TTPolBR1. The conditions for PCRs and the purification procedure were as described in Example 3-(1). The nucleotide sequences of the amplified fragments TPPolBF1-TTPolBR4 (about 1.2 kb), TPPolBF1-TTPolBR5 (about 1 kb) and TPPolBF5-TTPolBR1 (about 2 kb) were determined by direct sequencing. As a result, it was shown that *Thermococcus siculi* DNA polymerase contains an intein sequence.

(2) Cloning of Upstream and Downstream Portions of DNA Polymerase Gene

Specific oligonucleotides Tsi01 (SEQ ID NO:25) for cloning the upstream portion and Tsi06 (SEQ ID NO:26) for cloning the downstream portion were synthesized on the basis of the nucleotide sequence determined in Example 5-(1).
PCRs were carried out using 1 ng of the *Thermococcus siculi* genomic DNA prepared in Example 2 as a template, as well as a combination of 10 pmol of Tsi01 or Tsi06 and 10 pmol of one of the 32 primers listed in Table 1. The conditions for PCRs and the purification procedure were as described in Example 3-(2). The amplification products were subjected to direct sequencing to screen for fragments containing the upstream region of the DNA polymerase of interest. As a result, it was shown that an about 2900-bp fragment Tsi011A contained the upstream portion of the DNA polymerase gene, and an about 400-bp fragment Tsi065B contained the downstream portion of the DNA polymerase gene.

(3) Construction of Plasmid for Expressing DNA Polymerase

It was shown that one intein sequence is contained in the sequence of *Thermococcus siculi* DNA polymerase. Then, a DNA polymerase gene from which the intein sequence was eliminated was constructed.
Oligonucleotides TsiNde, TsiA, TsiB and TsiBamPst (SEQ ID NOS:27-30) were synthesized on the basis of the sequence determined in Example 5-(2).
PCRs were carried out in volumes of 100 µl using 100 ng of the *Thermococcus siculi* genomic DNA prepared in Example 2 as a template, as well as a combination of primers (20 pmol each) TksNde and TsiB (TsiI) or TsiA and TsiBamPst (TsiII). PCRs were carried out as described in Example 5-(2) to obtain DNA fragments TsiI (about 1.5. kb) and TsiII (about 0.9 kb). In addition, a PCR was carried out in a similar manner in a volume of 100 µl using a mixture of 1 µl of the PCR reaction mixture TsiI and 1 µl of the PCR reaction mixture TsiII as a template as well as 20 pmol of TsiNde and 20 pmol of TsiBamPst as primers. Then, an about 2.4-kb DNA fragment was obtained.
The resulting about 2.4-kb DNA fragment was digested with restriction enzymes NdeI and BamHI. The DNA fragment was ligated to pTV119Nd (a plasmid in which the NcoI site in pTV119N is converted into a NdeI site) which had been digested with NdeI and BamHI to construct a plasmid pTsi16. This plasmid is designated and indicated as pTsi16, and deposited on May 14, 2004 (date of original deposit) at International Patent Organism Depositary, National Institute of Advanced Industrial Science and Technology, AIST Tsukuba Central 6, 1-1, Higashi 1-Chome, Tsukuba-shi, Ibaraki-ken 305-8566, Japan under accession number FERM BP-10310.

(4) Determination of Nucleotide Sequence of DNA Fragment Containing DNA Polymerase Gene The nucleotide sequences of the DNA fragment inserted into pTsi16 obtained in Example 5-(3) was determined according to a dideoxy method. Analysis of the determined nucleotide sequence revealed the existence of an open reading frame presumably encoding a DNA polymerase of interest. The nucleotide sequence of the open reading frame is shown in SEQ ID NO:31. The amino acid sequence of DNA polymerase deduced from the nucleotide sequence is shown in SEQ ID NO:32.

(5) Expression of *Thermococcus Siculi* DNA Polymerase Gene

*Escherichia coli* JM109 transformed with the plasmid pTsi16 was cultured according to the method as described in Example 3-(6). Cells collected by centrifugation were suspended in 52 μl of sonication buffer and sonicated. A supernatant obtained by centrifuging the sonicated suspension at 12,000 rpm for 10 minutes was heated at 80° C. for 10 minutes and then centrifuged again at 12,000 rpm for 10 minutes to collect a supernatant as a heated supernatant.

The enzymatic activity of the heated supernatant was measured according to the method as described in Example 1. As a result, a DNA polymerase activity was observed.

(6) Preparation of Purified DNA Polymerase Preparation

*Escherichia coli* JM109 transformed with the plasmid pTsi16 was cultured according to the method as described in Example 3-(7). Purification was carried out following the procedure as described in Example 3-(7).

The thus obtained DNA polymerase was used as Tsi DNA polymerase preparation. The activity of the Tsi DNA polymerase preparation was measured according to the method as described in Example 1. As a result, a DNA polymerase activity was observed for the Tsi DNA polymerase preparation.

Example 6

(1) Incorporation and Extension Activities of Respective DNA Polymerases

Incorporation and extension activities of Tks, Tce and Tsi DNA polymerases were measured. A commercially available product NOD DNA polymerase (Toyobo) was used as a control.

When incorporation activities were measured, 1 μg of activated calf thymus DNA was used as a template. When extension activities were measured, M13/HT Primer in which 1 μg of M13 phage single-stranded DNA was annealed to 1 pmol of HT Primer (SEQ ID NO:33), which is complementary thereto, was used. KOD#1 buffer containing 1 mM magnesium chloride was used as a buffer. A DNA polymerase activity was measured as follows.

Briefly, 50 μl of KOD#1 buffer (Toyobo) containing an enzyme sample to be subjected to activity measurement, the above-mentioned template, 40 μM dNTP, 0.238 μM [$^3$H] methyl-TTP (Amersham) and 1 mM magnesium chloride was reacted at 75° C. for 5 minutes. 40 μl of the reaction mixture was spotted onto DE81 paper (Whatman). After washing with 5% $Na_2PO_4$ four times, the radioactivity remaining on DE81 paper was measured using a liquid scintillation counter. An amount of an enzyme that results in incorporation of 10 nmol of dNMP into a substrate DNA in minutes according to the above-mentioned enzymatic activity measurement method was defined as 1 U of the enzyme. The results are shown in Table 2. In Table 2, "incorporation" represents the ability to incorporate at nicked sites in a nucleic acid as a template, and "extension" represents the ability to incorporate due to extension from a primer annealed to a nucleic acid as a template.

TABLE 2

| Polymerase activity (U/μl) | Incorporation | Extension | Extension/ Incorporation |
| --- | --- | --- | --- |
| Tks | 9.38 | 11.46 | 1.22 |
| Tce | 10.83 | 13.28 | 1.23 |
| Tsi | 9.67 | 21.93 | 2.27 |
| KOD | 6.80 | 6.69 | 0.98 |

As shown in Table 2, it was confirmed that Tks, Tce and Tsi DNA polymerases exhibit activities of incorporation due to primer extension higher than activities of nucleic acid incorporation into a template DNA in KOD#1 buffer. Furthermore, it was confirmed that their activities of incorporation due to primer extension are very high as compared with KOD DNA polymerase used as a control. Based on the above, it was confirmed that the DNA polymerases of the present invention are very suitable for primer extension.

(2) Affinities to M13 Single-Stranded DNA

Incorporation and affinities to M13 single-stranded DNA polymerase were examined for Tks, Tce and Tsi DNA polymerases. KOD DNA polymerase was used as a control.

M13 single-stranded DNA at various concentrations was used as a template. 1 pmol of HT Primer which is complementary thereto was used as a primer. KOD#1 buffer containing 1 mM magnesium chloride was used as a buffer. DNA polymerase activities were measured according to the method as described in Example 6-(1). The results are shown in Table 3.

TABLE 3

| Polymerase | Km (μg/ml) |
| --- | --- |
| Tks | 1.04 |
| Tce | 0.91 |
| Tsi | 1.33 |
| KOD | 2.65 |

As shown in Table 3, it was confirmed that Tks,
Tce and Tsi DNA polymerases the present invention exhibit very higher affinities to M13 single-stranded DNA than KOD DNA polymerase. Based on the above, it was suggested that the DNA polymerases of the present invention are superior to KOD DNA polymerase in view of detection sensitivity in PCR.

(3) Fidelities of Tks and Tsi DNA Polymerases

Fidelities of Tks and Tsi DNA polymerases were examined. KOD DNA polymerase and KOD plus DNA polymerase (both from Toyobo) as well as Pyrobest DNA polymerase (Takara Bio) were used as controls.

*Thermus thermophilus* HB8 genomic DNA (Takara Bio) was used as a template. In addition, primers c280/RG34-F and -R (SEQ ID NOS:34 and 35) were used.

Fidelities were determined as follows. Briefly, PCRs were carried out in a volume of 50 µl using 10 ng of *Thermus thermophilus* HB8 genomic DNA as a template, as well as a combination of the primers c280/RG34-F and -R. Since the GC content of the region amplified using the pair of primers is high (70%), DMSO was added at a concentration of 2%. When Tks, Tsi and KOD plus DNA polymerases were used, KOD plus buffer was used according to the attached protocol. When KOD DNA polymerase was used, KOD#1 buffer was used according to the protocol attached to KOD DNA polymerase. Furthermore, Pyrobest DNA polymerase was used in the attached buffer according to the attached protocol. The conditions for the PCRs were as follows: incubation at 96° C. for 2 minutes followed by 30 cycles of 98° C. for 5 seconds; and 68° C. for 30 seconds. After reaction, equal volumes of a mixture of phenol saturated with 100 mM Tris-hydrochloride buffer (pH 8.0)/chloroform/isoamyl alcohol (25:24:1, v/v) were added thereto. The mixtures were mixed and then centrifuged at 10,000×g for 10 minutes twice. After centrifugation, the supernatants were mixed with a mixture of chloroform/isoamyl alcohol (24:1, v/v) and then centrifuged at 10,000×g for 10 minutes. The thus obtained supernatants were subjected to ethanol precipitation, and the precipitates were dissolved in 20 µl of $H_2O$ to obtain an about 0.5-bp DNA fragments. 8 µl each of the about 0.5-bp DNA fragments was treated according to the protocol of TaKaRa BKL Kit (Takara Bio), and 5 µl each of the resulting solutions was used to transform *Escherichia coli* JM109. The resulting transformants were cultured, nucleotide sequences were determined for 12-24 clones into which the about 500-bp DNA fragments were inserted, and the ratios of numbers of mutated nucleotides to numbers of read total nucleotides were calculated to determine fidelities. The results are shown in Table 4.

TABLE 4

| Buffer | Enzyme name | Mutation frequency |
|---|---|---|
| KOD plus | Tks | 0.000% |
|  | Tsi | 0.021% |
|  | KOD plus | 0.082% |
| Special buffer | Pyrobest | 0.023% |
| KOD#1 | KOD | 0.022% |

As shown in Table 4, it was confirmed that the mutation frequencies for Tks and Tsi DNA polymerases of the present invention were less than that for KOD, KOD plus or Pyrobest DNA polymerase. Based on the above, it was shown that they are more excellent as enzymes for cloning than KOD, KOD plus or Pyrobest DNA polymerase.

(4) Fidelities of Tks and Tce DNA Polymerases

Fidelities of Tks and Tce DNA polymerases were examined. KOD DNA polymerase and KOD plus DNA polymerase (both from Toyobo) as well as Pyrobest DNA polymerase (Takara Bio) were used as controls.

*Thermus thermophilus* HB8 genomic DNA (Takara Bio) was used as a template. In addition, primers c240/RA18-F and -R (SEQ ID NOS:36 and 37) were used.

For determining fidelities, PCRs were carried out in a volume of 50 µl using 10 ng of *Thermus thermophilus* HB-8 genomic DNA as a template, as well as a combination of the primers c240/RA18-F and -R. Since the GC content of the region amplified using the pair of primers is high (70%), DMSO was added at a concentration of 2%. KOD#1 buffer was used as a buffer according to the attached protocol. The conditions for the PCRs and the method for calculating fidelities were as described in Example 6-(3). The results are shown in Table 5.

TABLE 5

| Buffer | Enzyme name | Mutation frequency |
|---|---|---|
| KOD#1 | Tks | 0.000% |
|  | Tce | 0.000% |
|  | ROD | 0.064% |

As shown in Table 5, it was confirmed that the mutation frequencies for Tks and Tce DNA polymerases of the present invention were less than that for KOD. Also based on the above, it was shown that they are excellent as enzymes for cloning.

Example 7

(1) Optimal Temperatures of Respective DNA Polymerases

Optimal temperatures of Tks, Tce and Tsi DNA polymerases were determined. 20 µg of activated calf thymus DNA was used as a template. The buffer attached to Pyrobest DNA polymerase was used as a buffer. A DNA polymerase activity was measured as follows.

First, 50 µl of a reaction mixture containing 5 mU (as calculated according to the incorporation activity measurement method as described in Example 6-(1)) of an enzyme sample to be subjected to activity measurement, the above-mentioned template, 200 µM dATP, 200 µM dGTP, 200 µM dCTP, 100 µM dTTP, 0.204 µM [$^3$H]methyl-TTP (Amersham) and 1× buffer attached to Pyrobest DNA polymerase (Takara Bio) was prepared. Reactions were carried out for 5 minutes at desired temperatures ranging from 65° C. to 85° C. using the respective enzyme samples. 40 µl each of the reaction mixtures was spotted onto DE81 paper (Whatman). After washing with 5% $Na_2PO_4$ four times, the radioactivities remaining on DE81 paper were measured using a liquid scintillation counter. The relationship between the activity measured according to the above-mentioned activity measurement method and the reaction temperature is illustrated in FIG. 1. In FIG. 1, the activity observed for the reaction at 85° C. is defined as 100%.

As shown in FIG. 1, Tks, Tce and Tsi DNA polymerases had optimal temperatures ranging from 75° C. to 85° C. when the activated calf thymus DNA was used as a template.

(2) Optimal pHs of Respective DNA Polymerases

Optimal pHs of Tics, Toe and Tsi DNA polymerases were determined. 10 µg of activated calf thymus DNA was used as a template. 120 mM Tris-HCl buffers of which the pHs at 75° C. had been adjusted to desired values ranging from pH 5.0 to pH 8.0 were used as buffers. A DNA polymerase activity was measured as follows.

Figure 2:
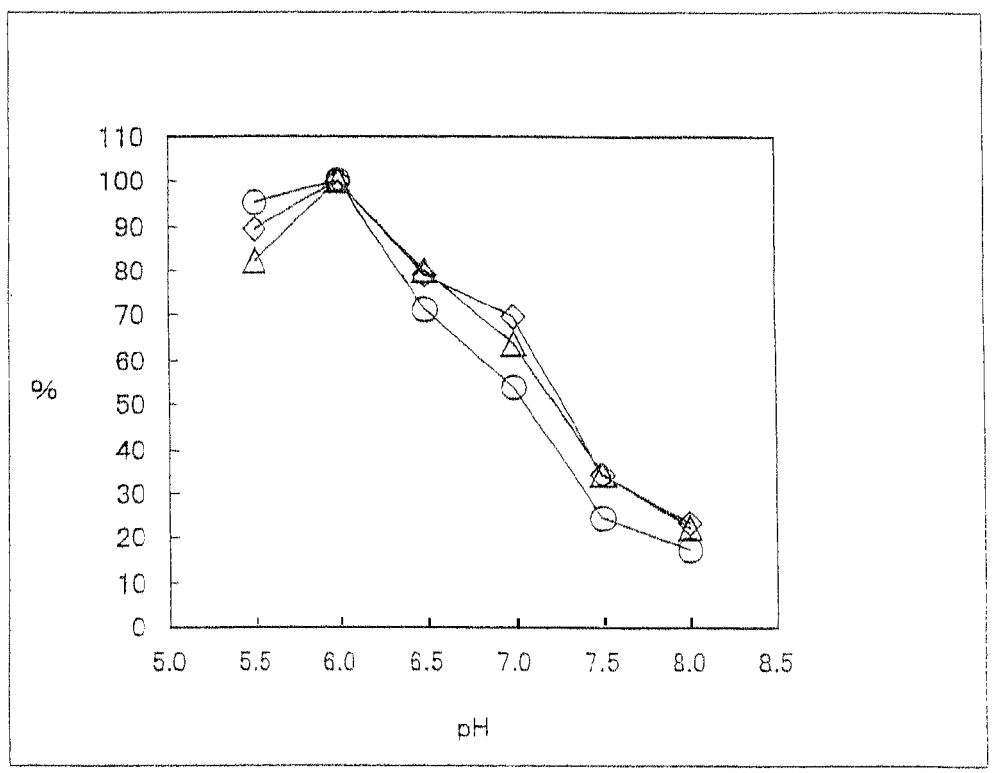
FIG. 2 illustrates the relationship between the DNA polymerase activity and the pH. In the figure, ◇, Δ and ○ represent results for Tks DNA polymerase, Tce DNA polymerase and Tsi DNA polymerase, respectively.

First, 50 µl of a reaction mixture containing 0.05 U (as calculated according to the incorporation activity measurement method as described in Example 6-(1)) of an enzyme sample to be subjected to activity measurement, the above-mentioned template, the above-mentioned buffer, 10 mM KCl, 6 mM $(NH_4)_2SO_4$, 0.1% Triton X-100, 0.001% BSA, 1 mM MCl$_2$, 40 μM dNTP and 0.204 μM [$^3$H]methyl-TTP (Amersham) was prepared. Reactions were carried out at 75° C. for 5 minutes using the respective enzyme samples. 40 μl each of the reaction mixtures was spotted onto DE81 paper (Whatman). After Na$_2$PO$_4$ four times, the washing with 5% radioactivities remaining on DE81 paper were measured using a liquid scintillation counter. The relationship between the activity measured according to the above-mentioned activity measurement method and the pH is illustrated in FIG. 2. In FIG. 2, the activity observed for the reaction at pH 6.0 (75° C.) is defined as 100%.

As shown in FIG. 2, Tks, Tce and Tsi DNA polymerases had optimal pHs ranging from pH 5.5 to pH 6.5 (75° C.) when the activated calf thymus DNA was used as a template.

Example 8

PCR reactions were carried out using 2-DNA as a template in order to compare the performances of the DNA polymerases of the present invention in PCR reactions with that of KOD DNA polymerase. 50 μl of a reaction mixture containing 1 ng/50 μl of λ-DNA (Takara Shuzo), 10 pmol/50 μl of a primer lambda-1, 10 pmol/50 μl of a primer lambda-9B and 0.625 U/50 μl of DNA polymerase was prepared with a reaction mixture composition of 1× buffer attached to KOD plus DNA polymerase, 200 μM dNTP and 1 mM (NH$_4$)$_2$SO$_4$ (for Tks, Tce or Tsi DNA polymerase); or 1× buffer attached to KOD DNA polymerase, 200 μM dNTP and 1 mM MgCl$_2$ (for KOD DNA polymerase).

The nucleotide sequences of the primers lambda-1 and lambda-9B are shown in SEQ ID NOS:38 and 39, respectively. The reaction mixtures were subjected to PCR reactions as follows: 30 cycles of 98° C. for 10 seconds; and 68° C. for 10 minutes. Then, 3 μl each of the reaction mixtures was subjected to agarose gel electrophoresis, and amplified DNA fragments were observed by staining with ethidium bromide. As a result, amplification of a DNA fragment was not observed using NOD DNA polymerase. On the other hand, amplification of a DNA fragment of about 12 kilobase pairs was observed using Tks, Tce or Tsi DNA polymerase.

Next, experiments were carried out changing the primers to a primer lambda-1 and a primer lambda-10D. The nucleotide sequence of the primer λ100 is shown in SEQ ID NO:40. 50 μl of a reaction mixture containing 1 ng/50 μl of λ-DNA (Takara Shuzo), 10 pmol/50 μl of the primer lambda-1, 10 pmol/50 μl of the primer lambda-10d and 0.625 U/50 μl of DNA polymerase was prepared with the same reaction mixture composition as the above. The reaction mixtures were subjected to PCR reactions as follows: 30 cycles of 98° C. for 10 seconds; and 68° C. for 10 minutes. Then, 3 μl each of the reaction mixtures was subjected to agarose gel electrophoresis, and amplified DNA fragments were observed by staining with ethidium bromide. As a result, amplification of a DNA fragment was not observed using KOD DNA polymerase. On the other hand, amplification of a DNA fragment of about 15 kilobase pairs was observed using Tks, Tce or Tsi DNA polymerase.

Example 9

(1) Production of Mouse Hybridoma Cell Lines

800 μl of PBS was added to 210 μg (100 μl) of the Tks DNA polymerase preparation prepared in Example 3, 210 μg (100 μl) of the Tce DNA polymerase preparation prepared in Example 4, or 200 μg (100 μl) of the Tsi DNA polymerase preparation prepared in Example 5. Each mixture was emulsified with 1 ml of complete Freund's adjuvant (Difco Lab.) to obtain an antigen preparation. The antigen preparation was divided into equal parts and intraperitoneally administered into four Balb/c mice (10 weeks old, female, CREA Japan). Booster immunization was carried out after 2 and 5 weeks as follows: an antigen preparation was prepared by adding 900 μl of PBS and RIBI Adjuvant (RIBI) to the same amount of the DNA polymerase preparation as the above, and equal parts thereof were intraperitoneally administered the respective mice. Furthermore, final immunization was carried out 6 weeks after the initial antigen administration as follows: an antigen preparation was prepared by adding 900 μl of PBS to the same amount of the DNA polymerase preparation as the above, and equals parts thereof were intraperitoneally administered to the mice in the respective groups.

Spleens were removed from two of the immunized animals 3 days after the final immunization, and subjected to cell fusion with P3-X63-Ag8-U1 mouse myeloma cells in the presence of 50% polyethylene glycol. The cells were dispensed into ten 96-well plates and cultured.

(2) Screening of Hybridoma Cell Lines

Solutions (5 μg/ml) of the respective DNA polymerase preparations used as antigens in Example 9-(1) were used to prepare 96-well plates coated with the DNA polymerases. For the cells obtained in the above-mentioned cell fusion, supernatants were collected from wells for which cell growth was observed, and the ELISA method was conducted on the DNA polymerase-coated plates to assay for the presence of anti-DNA polymerase antibodies in the culture supernatants. This assay was carried out for 900 or more cell lines obtained using the DNA polymerases as antigens. Lines judged to produce antibodies according to this procedure (Tks DNA polymerase: 95 lines; Tce DNA polymerase: 103 lines; Tsi DNA polymerase: 61 lines) were selected.

The selected cell lines as original cell lines were cultured, and inhibition of polymerase activities of the respective DNA polymerases was examined at 42° C. using the culture supernatants. Inhibitory activities were measured according to the following method. Anti-mouse IgG magnet beads (Dynabeads M-280 Sheep anti-Mouse IgG, Dynal Biotech) to which IgG in the culture supernatant from each hybridoma had been bound were incubated with the DNA polymerase at room temperature for 10 minutes. The DNA polymerase activity was then measured at 42° C. and compared with the results of DNA polymerase activity measurement using the DNA polymerase alone. As a result, inhibition of DNA polymerase activities was observed in culture supernatants from the following lines: Tks DNA polymerase: 18 lines; Tce DNA polymerase: 28 lines; Tsi DNA polymerase: 11 lines. These cell lines were subjected to cloning by limiting dilution analysis.

Inhibition of polymerase activity of the DNA polymerase at 42° C. by the culture supernatant from each cloned cell was examined. The following lines were selected as hybridoma clone lines that inhibit 95% or more of the polymerase activity: Tks DNA polymerase: 1 line; Tce DNA polymerase: 2 lines; Tsi DNA polymerase: 2 lines. The isotypes of antibodies produced by these hybridoma clone lines were examined. As a result, the antibodies to Tks and Tce DNA polymerases were of IgG2b type, and the antibodies to Tsi DNA polymerase were of IgG1 and G2b types. The activities of inhibiting the DNA polymerases were completely lost when the antibodies prepared from the culture supernatants from the hybridomas were heated at 94° C. for 5 minutes. Thus, it was shown that these antibodies can be used to inhibit activities of thermostable DNA polymerases in a low temperature-specific manner.

INDUSTRIAL APPLICABILITY

The present invention provides a polypeptide having a high-fidelity DNA polymerase activity suitable for primer extension which is useful for cloning, sequencing and nucleic acid amplification, a gene encoding the polypeptide, and a method for producing the polypeptide having a DNA polymerase activity. Using the polypeptide having a DNA polymerase activity of the present invention, it is possible to obtain an amplification product with a less error rate even if it is used in PCR comprising many cycles, for example. Thus, it is useful for analysis or identification of a target nucleic acid present at low copy number.

SEQUENCE LISTING FREE TEXT

SEQ ID No:1; Designed oligonucleotide primer TPPolBF4 to amplify a genomic DNA of *Thermococcus* sp.
SEQ ID No:2; Designed oligonucleotide primer TPPolBF5 to amplify a genomic DNA of *Thermococcus* sp.
SEQ ID No:3; Designed oligonucleotide primer TTPolBR1 to amplify a genomic DNA of *Thermococcus* sp.
SEQ ID No:4; Designed oligonucleotide primer TTPolBR4 to amplify a genomic DNA of *Thermococcus* sp.
SEQ ID No:5; Designed oligonucleotide primer Tks01 to amplify a genomic DNA of *Thermococcus* sp. KS-1
SEQ ID No:6; Designed oligonucleotide Tag sequence region to amplify a genomic DNA of *Thermococcus* sp.
SEQ ID No:7; Designed oligonucleotide primer Tks04 to amplify a genomic DNA of *Thermococcus* sp. KS-1
SEQ ID No:8; Designed oligonucleotide primer Tks02 to amplify a genomic DNA of *Thermococcus* sp. KS-1
SEQ ID No:9; Designed oligonucleotide primer TksNde to amplify a genomic DNA of *Thermococcus* sp. KS-1
SEQ ID No:10; Designed oligonucleotide primer Tks1EndBg to amplify a genomic DNA of *Thermococcus* sp. KS-1
SEQ ID No:11; Designed oligonucleotide primer Tks2StaBg to amplify a genomic DNA of *Thermococcus* sp. KS-1
SEQ ID No:12; Designed oligonucleotide primer Tks2EndBal to amplify a genomic DNA of *Thermococcus* sp. KS-1
SEQ ID No:13; Designed oligonucleotide primer Tks3StaBal to amplify a genomic DNA of *Thermococcus* sp. KS-1
SEQ ID No:14; Designed oligonucleotide primer TksBgPs to amplify a genomic DNA of *Thermococcus* sp. KS-1
SEQ ID No:17; Designed oligonucleotide primer TPPolBF1 to amplify a genomic DNA of *Thermococcus* sp.
SEQ ID No:18; Designed oligonucleotide primer TTPolBR5 to amplify a genomic DNA of *Thermococcus* sp.
SEQ ID No:19; Designed oligonucleotide primer Tce01 to amplify a genomic DNA of *Thermococcus celer*
SEQ ID No:20; Designed oligonucleotide primer Tce02 to amplify a genomic DNA of *Thermococcus celer*
SEQ ID No:21; Designed oligonucleotide primer TceNde to amplify a genomic DNA of *Thermococcus celer*
SEQ ID No:22; Designed oligonucleotide primer TceBgPs to amplify a genomic DNA of *Thermococcus celer*
SEQ ID No:25; Designed oligonucleotide primer Tsi01 to amplify a genomic DNA of *Thermococcus siculi*
SEQ ID No:26; Designed oligonucleotide primer Tsi06 to amplify a genomic DNA of *Thermococcus siculi*
SEQ ID No:27; Designed oligonucleotide primer TsiNde to amplify a genomic DNA of *Thermococcus siculi*
SEQ ID No:28; Designed oligonucleotide primer TsiA to amplify a genomic DNA of *Thermococcus siculi*
SEQ ID No:29; Designed oligonucleotide primer TsiB to amplify a genomic DNA of *Thermococcus siculi*
SEQ ID No:30; Designed oligonucleotide primer TsiBamPst to amplify a genomic DNA of *Thermococcus siculi*
SEQ ID No:33; Designed oligonucleotide primer HT to amplify a genomic DNA of M13SEQ ID No:34; Designed oligonucleotide primer c280/RG34-F to amplify a genomic DNA of *Thermus thermophilus* HB-8
SEQ ID No:35; Designed oligonucleotide primer c280/RG34-R to amplify a genomic DNA of *Thermus thermophilus* HB-8
SEQ ID No:36; Designed oligonucleotide primer c240/RA18-F to amplify a genomic DNA of *Thermus thermophilus* HB-8
SEQ ID No:37; Designed oligonucleotide primer c240/RA18-R to amplify a genomic DNA of *Thermus thermophilus* HB-8
SEQ ID No:38; Designed oligonucleotide primer lambda-1 to amplify a DNA of bacteriophage lambda
SEQ ID No:39; Designed oligonucleotide primer lambda-9B to amplify a DNA of bacteriophage lambda
SEQ ID No:40; Designed oligonucleotide primer lambda-10D to amplify a DNA of bacteriophage lambda

The invention claimed is:

1. An isolated polypeptide having a DNA polymerase activity, which comprises an amino acid sequence selected from the group consisting of:
   (a) the amino acid sequence of SEQ ID NO:32; and
   (b) an amino acid sequence which differs from SEQ ID NO:32 by deletion, insertion or substitution of a total of 1 to 10 amino acids.

2. The polypeptide of claim 1, wherein the amino acid sequence of (b) differs from SEQ ID NO:32 solely by substitution of 1-10 amino acid residues.

3. The polypeptide of claim 1, wherein the amino acid sequence of (b) differs from SEQ ID NO:32 by a single amino acid deletion, insertion or substitution.

4. The polypeptide of claim 1, wherein the amino acid sequence of (b) differs from SEQ ID NO:32 by a single amino acid substitution.

5. The polypeptide of claim 1 that comprises the amino acid sequence of SEQ ID NO:32.

6. The polypeptide of claim 1 that consists of the amino acid sequence of SEQ ID NO:32.

7. A composition for amplifying a nucleic acid, which comprises the polypeptide defined by claim 1.

8. A kit which comprises the polypeptide defined by claim 1.

9. A method for producing a polypeptide having DNA polymerase activity, the method comprising:
   culturing a cell capable of producing the polypeptide of claim 1, and
   collecting said polypeptide from the culture.

10. A method for amplifying a nucleic acid, the method comprising:
   amplifying a nucleic acid using the polypeptide of claim 1.

* * * * *

SEQUENCE LISTING

```
<160> NUMBER OF SEQ ID NOS: 40

<210> SEQ ID NO 1
<211> LENGTH: 40
<212> TYPE: DNA
<213> ORGANISM: Artificial Sequence
<220> FEATURE:
<223> OTHER INFORMATION: Designed oligonucleotide primer TPPolBF4 to
      amplify a genomic DNA of Thermococcus sp.
<220> FEATURE:
<221> NAME/KEY: misc_feature
<222> LOCATION: (35)..(35)
<223> OTHER INFORMATION: n stands for any base

<400> SEQUENCE: 1
ttaatacgac tcactatagg cacaacgtct crccngayac                           40
```

<210> SEQ ID NO 2
<211> LENGTH: 40
<212> TYPE: DNA
<213> ORGANISM: Artificial Sequence
<220> FEATURE:
<223> OTHER INFORMATION: Designed oligonucleotide primer TPPolBF5 to amplify a genomic DNA of Thermococcus sp.
<220> FEATURE:
<221> NAME/KEY: misc_feature
<222> LOCATION: (32)..(32)
<223> OTHER INFORMATION: n stands for any base
<220> FEATURE:
<221> NAME/KEY: misc_feature
<222> LOCATION: (35)..(35)
<223> OTHER INFORMATION: n stands for any base

<400> SEQUENCE: 2
ttaatacgac tcactatagg gagagcgtta cngcntgggg    40

<210> SEQ ID NO 3
<211> LENGTH: 39
<212> TYPE: DNA
<213> ORGANISM: Artificial Sequence
<220> FEATURE:
<223> OTHER INFORMATION: Designed oligonucleotide primer TTPolBR1 to amplify a genomic DNA of Thermococcus sp.

<400> SEQUENCE: 3
gctagttatt gctcagcgga cctggttctc katrtarta    39

<210> SEQ ID NO 4
<211> LENGTH: 39
<212> TYPE: DNA
<213> ORGANISM: Artificial Sequence
<220> FEATURE:
<223> OTHER INFORMATION: Designed oligonucleotide primer TTPolBR4 to amplify a genomic DNA of Thermococcus sp.

<400> SEQUENCE: 4
gctagttatt gctcagcggg taacgctctc kgcrcaytc    39

<210> SEQ ID NO 5
<211> LENGTH: 21
<212> TYPE: DNA
<213> ORGANISM: Artificial Sequence
<220> FEATURE:
<223> OTHER INFORMATION: Designed oligonucleotide primer Tks01 to amplify a genomic DNA of Thermococcus sp. KS-1

<400> SEQUENCE: 5
cttcatcttc ttctttatct t    21

<210> SEQ ID NO 6
<211> LENGTH: 16
<212> TYPE: DNA
<213> ORGANISM: Artificial Sequence
<220> FEATURE:
<223> OTHER INFORMATION: Designed oligonucleotide Tag sequence region to amplify a genomic DNA of Thermococcus sp.

<400> SEQUENCE: 6
ttacgtctga cgtgtg    16

<210> SEQ ID NO 7
<211> LENGTH: 21
<212> TYPE: DNA
<213> ORGANISM: Artificial Sequence
<220> FEATURE:

<223> OTHER INFORMATION: Designed oligonucleotide primer Tks04 to
      amplify a genomic DNA of Thermococcus sp. KS-1

<400> SEQUENCE: 7
attcccatac ttttctaact c                                          21

<210> SEQ ID NO 8
<211> LENGTH: 21
<212> TYPE: DNA
<213> ORGANISM: Artificial Sequence
<220> FEATURE:
<223> OTHER INFORMATION: Designed oligonucleotide primer Tks02 to
      amplify a genomic DNA of Thermococcus sp. KS-1

<400> SEQUENCE: 8
accggtcccc acgttgccgt t                                          21

<210> SEQ ID NO 9
<211> LENGTH: 36
<212> TYPE: DNA
<213> ORGANISM: Artificial Sequence
<220> FEATURE:
<223> OTHER INFORMATION: Designed oligonucleotide primer TksNde to
      amplify a genomic DNA of Thermococcus sp. KS-1

<400> SEQUENCE: 9
gattatgggg gatgacatat gatcctcgac actgac                          36

<210> SEQ ID NO 10
<211> LENGTH: 33
<212> TYPE: DNA
<213> ORGANISM: Artificial Sequence
<220> FEATURE:
<223> OTHER INFORMATION: Designed oligonucleotide primer Tks1EndBg to
      amplify a genomic DNA of Thermococcus sp. KS-1

<400> SEQUENCE: 10
ggggtacaga gatctaaaat ctaggtacac tat                             33

<210> SEQ ID NO 11
<211> LENGTH: 40
<212> TYPE: DNA
<213> ORGANISM: Artificial Sequence
<220> FEATURE:
<223> OTHER INFORMATION: Designed oligonucleotide primer Tks2StaBg to
      amplify a genomic DNA of Thermococcus sp. KS-1

<400> SEQUENCE: 11
gtacctagat tttagatctc tgtacccctc aatcatcatc                      40

<210> SEQ ID NO 12
<211> LENGTH: 33
<212> TYPE: DNA
<213> ORGANISM: Artificial Sequence
<220> FEATURE:
<223> OTHER INFORMATION: Designed oligonucleotide primer Tks2EndBal to
      amplify a genomic DNA of Thermococcus sp. KS-1

<400> SEQUENCE: 12
gtagccgtag tagctgttgg ccaggatctt gat                             33

<210> SEQ ID NO 13
<211> LENGTH: 40
<212> TYPE: DNA
<213> ORGANISM: Artificial Sequence
<220> FEATURE:
<223> OTHER INFORMATION: Designed oligonucleotide primer Tks3StaBal to
      amplify a genomic DNA of Thermococcus sp. KS-1

<400> SEQUENCE: 13
atcaagatcc tggccaacag ctactacggt tactacggct          40

<210> SEQ ID NO 14
<211> LENGTH: 39
<212> TYPE: DNA
<213> ORGANISM: Artificial Sequence
<220> FEATURE:
<223> OTHER INFORMATION: Designed oligonucleotide primer TksBgPs to
      amplify a genomic DNA of Thermococcus sp. KS-1

<400> SEQUENCE: 14
tccgctggaa aacctgcaga gatctcaagt tcccttcgg           39

<210> SEQ ID NO 15
<211> LENGTH: 2325
<212> TYPE: DNA
<213> ORGANISM: Thermococcus sp. KS-1

<400> SEQUENCE: 15
atgatcctcg acactgacta cataactgag aatggaaaac ccgtcataag gattttcaag      60
aaggagaacg gcgagtttaa gattgagtac gataggactt ttgaacccta catttacgcc    120
ctcctgaagg acgattctgc cattgaggag gtcaagaaga taaccgccga gaggcacgga    180
acggttgtaa cggttaagcg ggctgaaaag gttcagaaga agttcctcgg gagaccagtt    240
gaggtctgga aactctactt tactcaccct caggacgtcc cagcgataag ggacaagata    300
cgagagcatc cagcagttat tgacatctac gagtacgaca taccccttcgc caagcgctac    360 ctcatagaca aggggattagt gccaatgaaa ggcgacgagg agctgaaaat gcttgccttt    420
gatatcgaga cgctctacca tgagggcgag gagttcgccg aggggccaat ccttatgata    480
agctacgccg acgaggaagg ggccagggtg ataacgtgga agaacgcgga tctgccctac    540
gttgacgtcg tctcgacgga gagggagatg ataaagcgct tcctaaaggt ggtcaaagag    600
aaagatcctg acgtcctaat aacctacaac ggcgacaact tcgacttcgc ctacctaaaa    660
aaacgctgtg aaaagcttgg aataaacttc acgctcggaa gggacggaag cgagccgaag    720
attcagagga tgggcgacag gtttgccgtc gaagtgaagg gacggataca cttcgatctc    780
tatcctgtga taagacggac gataaacctg cccacataca cgcttgaggc cgtttatgaa    840
gccgtcttcg gtcagccgaa ggagaaggtc tacgctgagg agatagctac agcttgggag    900
agcggtgaag gccttgagag agtagccaga tactcgatgg aagatgcgaa ggtcacatac    960
gagcttggga aggagttttt ccctatggag gcccagcttt ctcgcttaat cggccagtcc   1020
ctctgggacg tctcccgctc cagcactggc aacctcgttg agtggttcct cctcaggaag   1080
gcctacgaga ggaatgagct ggccccgaac aagcccgatg aaaaggagct ggccagaaga   1140
cgacagagct atgaaggagg ctatgtaaaa gagcccgaga gagggttgtg ggagaacata   1200
gtgtacctag attttagatc tctgtacccc tcaatcatca tcacccacaa cgtctcgccg   1260
gatactctca caggggaagg atgcaaggaa tatgacgttg cccccaggt cggtcaccgc    1320 ttctgcaagg acttcccagg atttatcccg agcctgcttg agacctcct agaggagagg    1380 cagaagataa agaagaagat gaaggccacg attgacccga tcgagaggaa gctcctcgat   1440
tacaggcaga gggccatcaa gatcctggcc aacagctact acggttacta cggctatgca   1500
agggcgcgct ggtactgcaa ggagtgtgca gagagcgtaa cggcctgggg aagggagtac   1560
ataacgatga ccatcagaga gatagaggaa aagtacggct ttaaggtaat ctacagcgac   1620

```
accgacggat tttttgccac aatacctgga gccgatgctg aaaccgtcaa aagaaggcg    1680
atggagttcc tcaagtatat caacgccaaa ctcccgggcg cgcttgagct cgagtacgag   1740
ggcttctaca acgcggctt cttcgtcacg aagaagaagt acgcggtgat agacgaggaa    1800
ggcaagataa caacgcgcgg acttgagatt gtgaggcgcg actggagcga gatagcgaaa   1860
gagacgcagg cgagggttct tgaagctttg ctaaaggacg gtgacgtcga aaggccgtg    1920
aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtctgggagc ctggctgaag ccgaagggaa cttga                   2325

<210> SEQ ID NO 16
<211> LENGTH: 774
<212> TYPE: PRT
<213> ORGANISM: Thermococcus sp. KS-1

<400> SEQUENCE: 16

Met Ile Leu Asp Thr Asp Tyr Ile Thr Glu Asn Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Ile Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Ala Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ala
                165                 170                 175

Asp Leu Pro Tyr Val Asp Val Val Ser Thr Glu Arg Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255
```

```
His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
            275                 280                 285

Lys Val Tyr Ala Glu Glu Ile Ala Thr Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Lys Glu Phe Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Arg Glu Ile
            515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685
```

Arg Gly Val Lys Ile Arg Pro Gly Thr Val Ile Ser Tyr Ile Val Leu
    690             695                 700

Lys Gly Ser Gly Arg Ile Gly Asp Arg Ala Ile Pro Phe Asp Glu Phe
705             710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Gly Ala Trp
        755                 760                 765

Leu Lys Pro Lys Gly Thr
    770

<210> SEQ ID NO 17
<211> LENGTH: 40
<212> TYPE: DNA
<213> ORGANISM: Artificial Sequence
<220> FEATURE:
<223> OTHER INFORMATION: Designed oligonucleotide primer TPPolBF1 to
      amplify a genomic DNA of Thermococcus sp.

<400> SEQUENCE: 17
ttaatacgac tcactatagg cgctacctca tmgayaargg                              40

<210> SEQ ID NO 18
<211> LENGTH: 39
<212> TYPE: DNA
<213> ORGANISM: Artificial Sequence
<220> FEATURE:
<223> OTHER INFORMATION: Designed oligonucleotide primer TTPolBR5 to
      amplify a genomic DNA of Thermococcus sp.

<400> SEQUENCE: 18
gctagttatt gctcagcggg tatctggyga gacrttrtg                               39

<210> SEQ ID NO 19
<211> LENGTH: 21
<212> TYPE: DNA
<213> ORGANISM: Artificial Sequence
<220> FEATURE:
<223> OTHER INFORMATION: Designed oligonucleotide primer Tce01 to
      amplify a genomic DNA of Thermococcus celer

<400> SEQUENCE: 19
cgtggtaaga gggtctcgaa t                                                  21

<210> SEQ ID NO 20
<211> LENGTH: 21
<212> TYPE: DNA
<213> ORGANISM: Artificial Sequence
<220> FEATURE:
<223> OTHER INFORMATION: Designed oligonucleotide primer Tce02 to
      amplify a genomic DNA of Thermococcus celer

<400> SEQUENCE: 20
ctcaagggct ccggaaggat a                                                  21

<210> SEQ ID NO 21
<211> LENGTH: 36
<212> TYPE: DNA
<213> ORGANISM: Artificial Sequence
<220> FEATURE:
<223> OTHER INFORMATION: Designed oligonucleotide primer TceNde to
      amplify a genomic DNA of Thermococcus celer

```
<400> SEQUENCE: 21
aatccaacgg gtggtcatat gatcctcgac gctgac                              36

<210> SEQ ID NO 22
<211> LENGTH: 39
<212> TYPE: DNA
<213> ORGANISM: Artificial Sequence
<220> FEATURE:
<223> OTHER INFORMATION: Designed oligonucleotide primer TceBgPs to
      amplify a genomic DNA of Thermococcus celer

<400> SEQUENCE: 22
cagagaggag catgcagatc ttcacccctt ccccgcgtt                           39

<210> SEQ ID NO 23
<211> LENGTH: 2325
<212> TYPE: DNA
<213> ORGANISM: Thermococcus celer

<400> SEQUENCE: 23
atgatcctcg acgctgacta catcaccgaa gatgggaagc ccgtcgtgag gatattcagg    60
aaggagaagg cgagttcag aatcgactac gacagggact tcgagcccta catctacgcc   120
ctcctgaagg acgattcggc catcgaggag gtgaagagga taaccgttga gcgccacggg   180
aaggccgtca gggttaagcg ggtggagaag gtcgaaaaga agttcctcaa caggccgata   240
gaggtctgga agctctactt caatcacccg caggacgttc cggcgataag ggacgagata   300
aggaagcatc cggccgtcgt tgatatctac gagtacgaca tccccttcgc caagcgctac   360
ctcatcgata aggggctcgt cccgatggag ggggaggagg agctcaaact gatggccttc   420
gacatcgaga ccctctacca cgagggagac gagttcgggg aggggccgat cctgatgata   480
agctacgccg acggggacgg ggcgagggtc ataacctgga agaagatcga cctcccctac   540
gtcgacgtcg tctcgaccga gaaggagatg ataaagcgct tcctccaggt ggtgaaggag   600
aaggacccgg acgtgctcgt aacttacaac ggcgacaact tcgacttcgc ctacctgaag   660
agacgctccg aggagcttgg attgaagttc atcctcggga gggacgggag cgagcccaag   720
atccagcgca tgggcgaccg cttcgccgtc gaggtgaagg ggaggataca cttcgacctc   780
tacccggtga taaggcgcac cgtgaacctg ccgacctaca cgctcgaggc ggtctacgag   840
gccatcttcg ggaggccaaa ggagaaggtc tacgccgggg agatagtgga ggcctgggaa   900
accggcgagg gtcttgagag ggttgcccgc tactccatgg aggacgcaaa ggttaccttc   960
gagctcggga gggagttctt cccgatggag gcccagctct cgaggctcat cggccagggt  1020
ctctgggacg tctcccgctc gagcaccggc aacctggtcg agtggttcct cctgaggaag  1080
gcctacgaga ggaacgaact ggcccccgaac aagccgagcg gccgggaagt ggagatcagg  1140
aggcgtggct acgccggtgg ttacgttaag gagccggaga ggggtttatg ggagaacatc  1200
gtgtacctcg actttcgctc tctttacccc tccatcatca taacccacaa cgtctcgccc  1260 gatacccctaa acagggaggg ctgtgagaac tacgacgtcg cccccccaggt ggggcataag  1320 ttctgcaaag attttccggg cttcatcccg agcctgctcg aggcctgct tgaggagagg  1380 cagaagataa agcggaggat gaaggcctct gtggatcccg ttgagcggaa gctcctcgat  1440
tacaggcaga gggccatcaa gatactggcc aacagcttct acggatacta cggctacgcg  1500
agggcgaggt ggtactgcag ggagtgcgcg gagagcgtta ccgcctgggg caggagtac   1560 atcgataggg tcatcaggga gctcgaggag aagttcggct tcaaggtgct ctacgcggac  1620
acggacggac tgcacgccac gatccccggg gcggacgccg ggaccgtcaa ggagagggcg  1680
```

```
agggggttcc tgagatacat caaccccaag ctccccggcc tcctggagct cgagtacgag   1740
gggttctacc tgaggggttt cttcgtgacg aagaagaagt acgcggtcat agacgaggag   1800
ggcaagataa ccacgcgcgg cctcgagata gtcaggcggg actggagcga ggtggccaag   1860
gagacgcagg cgagggtcct ggaggcgata ctgaggcacg gtgacgtcga ggaggccgtt   1920
agaatcgtca gggaggtaac cgaaaagctg agcaagtacg aggttccgcc ggagaaactg   1980
gtgatccacg agcagataac gagggatttg agggactaca aagccacggg accgcacgtg   2040
gcggtggcga agcgcctggc cgggagggggg gtaaggatac gccccgggac ggtgataagc   2100
tacatcgtcc tcaagggctc cggaaggata ggggacaggg cgattcccttt cgacgagttc   2160 gacccgacta agcacaggta cgacgccgac tactacatcg agaaccaggt tctgccagcc   2220
gtcgagagga tcctgaaggc cttcggctac cgcaaggagg acctgaaata ccagaagacg   2280
aggcaggtgg gcctgggtgc gtggctcaac gcggggaagg ggtga             2325
```

<210> SEQ ID NO 24
<211> LENGTH: 774
<212> TYPE: PRT
<213> ORGANISM: Thermococcus celer

<400> SEQUENCE: 24

```
Met Ile Leu Asp Ala Asp Tyr Ile Thr Glu Asp Gly Lys Pro Val Val
1               5                   10                  15

Arg Ile Phe Arg Lys Glu Lys Gly Glu Phe Arg Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Glu Val Lys Arg Ile Thr Val Glu Arg His Gly Lys Ala Val Arg
    50                  55                  60

Val Lys Arg Val Glu Lys Val Glu Lys Lys Phe Leu Asn Arg Pro Ile
65                  70                  75                  80

Glu Val Trp Lys Leu Tyr Phe Asn His Pro Gln Asp Val Pro Ala Ile
                85                  90                  95

Arg Asp Glu Ile Arg Lys His Pro Ala Val Val Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Glu Glu Glu Leu Lys Leu Met Ala Phe Asp Ile Glu Thr
    130                 135                 140

Leu Tyr His Glu Gly Asp Glu Phe Gly Glu Gly Pro Ile Leu Met Ile
145                 150                 155                 160

Ser Tyr Ala Asp Gly Asp Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Gln Val Val Lys Glu Lys Asp Pro Asp Val Leu Val Thr
        195                 200                 205

Tyr Asn Gly Asp Asn Phe Asp Phe Ala Tyr Leu Lys Arg Arg Ser Glu
    210                 215                 220

Glu Leu Gly Leu Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Val Asn Leu Pro Thr
```

-continued

```
                260                 265                 270
Tyr Thr Leu Glu Ala Val Tyr Glu Ala Ile Phe Gly Arg Pro Lys Glu
            275                 280                 285
Lys Val Tyr Ala Gly Glu Ile Val Glu Ala Trp Glu Thr Gly Glu Gly
            290                 295                 300
Leu Glu Arg Val Ala Arg Tyr Ser Met Glu Asp Ala Lys Val Thr Phe
305                 310                 315                 320
Glu Leu Gly Arg Glu Phe Phe Pro Met Glu Ala Gln Leu Ser Arg Leu
                325                 330                 335
Ile Gly Gln Gly Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Ser Gly Arg Glu Val Glu Ile Arg Arg Gly Tyr
            370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Glu Asn Tyr Asp
            420                 425                 430
Val Ala Pro Gln Val Gly His Lys Phe Cys Lys Asp Phe Pro Gly Phe
            435                 440                 445
Ile Pro Ser Leu Leu Gly Gly Leu Leu Glu Glu Arg Gln Lys Ile Lys
            450                 455                 460
Arg Arg Met Lys Ala Ser Val Asp Pro Val Glu Arg Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Arg Ala Arg Trp Tyr Cys Arg Glu Cys Ala Glu Ser
            500                 505                 510
Val Thr Ala Trp Gly Arg Glu Tyr Ile Asp Arg Val Ile Arg Glu Leu
            515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Gly Thr Val Lys Glu Arg Ala
545                 550                 555                 560
Arg Gly Phe Leu Arg Tyr Ile Asn Pro Lys Leu Pro Gly Leu Leu Glu
                565                 570                 575
Leu Glu Tyr Glu Gly Phe Tyr Leu Arg Gly Phe Phe Val Thr Lys Lys
            580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Val Ala Lys Thr Gln Ala
            610                 615                 620
Arg Val Leu Glu Ala Ile Leu Arg His Gly Asp Val Glu Glu Ala Val
625                 630                 635                 640
Arg Ile Val Arg Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Gly
            675                 680                 685
```

```
Arg Gly Val Arg Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Asp Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Lys Tyr Gln Lys Thr Arg Gln Val Gly Leu Gly Ala Trp
        755                 760                 765

Leu Asn Ala Gly Lys Gly
    770

<210> SEQ ID NO 25
<211> LENGTH: 21
<212> TYPE: DNA
<213> ORGANISM: Artificial Sequence
<220> FEATURE:
<223> OTHER INFORMATION: Designed oligonucleotide primer Tsi01 to
      amplify a genomic DNA of Thermococcus siculi

<400> SEQUENCE: 25
ctcatggtag agcgtctcaa t                                            21

<210> SEQ ID NO 26
<211> LENGTH: 21
<212> TYPE: DNA
<213> ORGANISM: Artificial Sequence
<220> FEATURE:
<223> OTHER INFORMATION: Designed oligonucleotide primer Tsi06 to
      amplify a genomic DNA of Thermococcus siculi

<400> SEQUENCE: 26
catcagctac atcgtgctca a                                            21

<210> SEQ ID NO 27
<211> LENGTH: 36
<212> TYPE: DNA
<213> ORGANISM: Artificial Sequence
<220> FEATURE:
<223> OTHER INFORMATION: Designed oligonucleotide primer TsiNde to
      amplify a genomic DNA of Thermococcus siculi

<400> SEQUENCE: 27
tacccggtgt cccatatgat cctcgacacg gactac                            36

<210> SEQ ID NO 28
<211> LENGTH: 33
<212> TYPE: DNA
<213> ORGANISM: Artificial Sequence
<220> FEATURE:
<223> OTHER INFORMATION: Designed oligonucleotide primer TsiA to amplify
      a genomic DNA of Thermococcus siculi

<400> SEQUENCE: 28
ctttatgcgg acactgacgg cttcttcgcg acg                               33

<210> SEQ ID NO 29
<211> LENGTH: 36
<212> TYPE: DNA
<213> ORGANISM: Artificial Sequence
<220> FEATURE:
<223> OTHER INFORMATION: Designed oligonucleotide primer TsiB to amplify
      a genomic DNA of Thermococcus siculi

<400> SEQUENCE: 29
```

```
gaagccgtca gtgtccgcat aaagtacttt aaagcc                                36
```

<210> SEQ ID NO 30
<211> LENGTH: 39
<212> TYPE: DNA
<213> ORGANISM: Artificial Sequence
<220> FEATURE:
<223> OTHER INFORMATION: Designed oligonucleotide primer TsiBamPst to
      amplify a genomic DNA of Thermococcus siculi

<400> SEQUENCE: 30

```
gttcacttgc tgcagggatc ctcacccctt ccccttcgg                             39
```

<210> SEQ ID NO 31
<211> LENGTH: 2328
<212> TYPE: DNA
<213> ORGANISM: Thermococcus siculi

<400> SEQUENCE: 31

```
atgatcctcg acacggacta catcacggaa gatgggaaac ccgtcataag gatattcaag      60
aaagagaacg gcgagttcaa gatcgagtac gacaggactt tgaacccta catctacgcc     120
ctcctgaagg acgactccgc gattgaggat gttaaaaaga taaccgccga gaggcacgga    180
acggtggtga aggtcaagcg cgccgaaaag gtgcagaaga agttcctagg caggccggtt    240
gaagtctgga agctctactt caccccacccc caagatgtcc cggcgataag ggacaagatt    300
aggaagcatc cagctgtaat tgacatctac gagtacgaca taccattcgc caagcgctac    360
ctcatcgaca agggcctgat tccgatggag ggtgaagaag agcttaagat gctcgccttc    420
gacattgaga cgctctacca tgagggtgag gagttcgccg aggggcctat tctgatgata    480
agctacgccg acgagagcga ggcacgcgtc atcacctgga gaaaatcga cctcccctac    540
gttgacgtcg tctcaacgga gaaggagatg ataaagcgct tcctccgcgt tgtgaaggag    600
aaagatcccg atgtcctcat aacctacaac ggcgacaact tcgacttcgc ctacctgaag    660
aagcgctgtg aaaagcttgg aataaacttc ctccttggaa gggacgggag cgagccgaag    720
atccagagaa tgggtgaccg cttcgccgtt gaggtgaagg ggaggataca cttcgacctc    780
tatcctgtaa taggcgcac gataaacctg ccgacctaca tgcttgaggc agtctacgag    840
gccatctttg ggaagccaaa ggagaaggtt tacgccgagg agatagccac cgcttgggaa    900
accggagagg gccttgagag ggtggctcgc tactctatgg aggacgcgaa ggtcacgttt    960
gagcttggaa aggagttctt cccgatggag gcccaacttt cgaggttggt cggccagagc   1020
ttctgggatg tcgcgcgctc aagcacgggc aatctggtcg agtggttcct cctcaggaag   1080
gcctacgaga ggaacgagct ggctccaaac aagccctctg gaagggaata tgacgagagg   1140
cgcggtggat acgccggcgg ctacgtcaag gaaccggaaa agggcctgtg ggagaacata   1200
gtctacctcg actataaatc tctctacccc tcaatcatca tcacccacaa cgtctcgccc   1260
gataccctca accgcgaggg ctgtaaggag tatgacgtag ctccacaggt cggccaccgc   1320
ttctgcaagg acttttccagg cttcatcccg agcctgctcg ggatctcct ggaggagagg   1380
cagaagataa agaggaagat gaaggcaaca attgacccga tcgagagaaa gctccttgat   1440
tacaggcaac gggccatcaa gatccttcta aatagttttt acggctacta cggctacgca   1500
agggctcgct ggtactgcaa ggagtgtgcc gagagcgtta cggcatgggg aagggaatat   1560
atcaccatga caatcaggga aatagaagag aagtatggct ttaaagtact ttatgcggac   1620
actgacggct tcttcgcgac gattcccggg gaagatgccg agaccatcaa aaagagggcg   1680
```

-continued

```
atggagttcc tcaagtacat aaacgccaaa ctccccggtg cgctcgaact tgagtacgag   1740
gacttctaca ggcgcggctt cttcgtcacc aagaagaaat acgcggttat cgacgaggag   1800
ggcaagataa caacgcgcgg gctggagatc gtcaggcgcg actggagcga gatagccaag   1860
gagacgcagg cgcgggttct ggaggccctt ctgaaggacg tgacgtcga agaggccgtg    1920 agcatagtca agaagtgac cgagaagctg agcaagtacg aggttccgcc ggagaagctc    1980
gttatccacg agcagataac gcgcgagctg aaggactaca aggcaacggg accacacgtg   2040
gcgatagcga agaggttagc cgcgagaggc gtcaaaatcc gccccgggac agtcatcagc   2100
tacatcgtgc tcaagggctc cggaggaata ggcgacaggg cgattccctt cgacgagttc   2160
gaccccacga agcacaagta cgatgcagag tactacatcg agaaccaggt tctacctgcc   2220
gtcgagagga ttctgaaggc cttcggctat cgcggtgagg agctcagata ccagaagacg   2280
aggcaggttg gacttggggc gtggctgaag ccgaagggga aggggtga               2328
```

<210> SEQ ID NO 32
<211> LENGTH: 775
<212> TYPE: PRT
<213> ORGANISM: Thermococcus siculi

<400> SEQUENCE: 32

```
Met Ile Leu Asp Thr Asp Tyr Ile Thr Glu Asp Gly Lys Pro Val Ile
  1               5                  10                  15

Arg Ile Phe Lys Lys Glu Asn Gly Glu Phe Lys Ile Glu Tyr Asp Arg
             20                  25                  30

Thr Phe Glu Pro Tyr Ile Tyr Ala Leu Leu Lys Asp Asp Ser Ala Ile
         35                  40                  45

Glu Asp Val Lys Lys Ile Thr Ala Glu Arg His Gly Thr Val Val Lys
     50                  55                  60

Val Lys Arg Ala Glu Lys Val Gln Lys Lys Phe Leu Gly Arg Pro Val
 65                  70                  75                  80

Glu Val Trp Lys Leu Tyr Phe Thr His Pro Gln Asp Val Pro Ala Ile
                 85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Leu Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270
```

```
Tyr Met Leu Glu Ala Val Tyr Glu Ala Ile Phe Gly Lys Pro Lys Glu
        275                 280                 285
Lys Val Tyr Ala Glu Glu Ile Ala Thr Ala Trp Glu Thr Gly Glu Gly
        290                 295                 300
Leu Glu Arg Val Ala Arg Tyr Ser Met Glu Asp Ala Lys Val Thr Phe
305                 310                 315                 320
Glu Leu Gly Lys Glu Phe Phe Pro Met Glu Ala Gln Leu Ser Arg Leu
                325                 330                 335
Val Gly Gln Ser Phe Trp Asp Val Ala Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Ser Gly Arg Glu Tyr Asp Glu Arg Arg Gly Gly Tyr
        370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
        450                 455                 460
Arg Lys Met Lys Ala Thr Ile Asp Pro Ile Glu Arg Lys Leu Leu Asp
465                 470                 475                 480
Tyr Arg Gln Arg Ala Ile Lys Ile Leu Leu Asn Ser Phe Tyr Gly Tyr
                485                 490                 495
Tyr Gly Tyr Ala Arg Ala Arg Trp Tyr Cys Lys Glu Cys Ala Glu Ser
                500                 505                 510
Val Thr Ala Trp Gly Arg Glu Tyr Ile Thr Met Thr Ile Arg Glu Ile
                515                 520                 525
Glu Glu Lys Tyr Gly Phe Lys Val Leu Tyr Ala Asp Thr Asp Gly Phe
        530                 535                 540
Phe Ala Thr Ile Pro Gly Glu Asp Ala Glu Thr Ile Lys Lys Arg Ala
545                 550                 555                 560
Met Glu Phe Leu Lys Tyr Ile Asn Ala Lys Leu Pro Gly Ala Leu Glu
                565                 570                 575
Leu Glu Tyr Glu Asp Phe Tyr Arg Arg Gly Phe Phe Val Thr Lys Lys
                580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
        610                 615                 620
Arg Val Leu Glu Ala Leu Leu Lys Asp Gly Asp Val Glu Glu Ala Val
625                 630                 635                 640
Ser Ile Val Lys Glu Val Thr Glu Lys Leu Ser Lys Tyr Glu Val Pro
                645                 650                 655
Pro Glu Lys Leu Val Ile His Glu Gln Ile Thr Arg Glu Leu Lys Asp
                660                 665                 670
Tyr Lys Ala Thr Gly Pro His Val Ala Ile Ala Lys Arg Leu Ala Ala
        675                 680                 685
Arg Gly Val Lys Ile Arg Pro Gly Thr Val Ile Ser Tyr Ile Val Leu
```

```
            690                 695                 700
Lys Gly Ser Gly Arg Ile Gly Asp Arg Ala Ile Pro Phe Asp Glu Phe
705                     710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Lys Ala Phe Gly Tyr Arg Gly
            740                 745                 750

Glu Glu Leu Arg Tyr Gln Lys Thr Arg Gln Val Gly Leu Gly Ala Trp
                755                 760                 765

Leu Lys Pro Lys Gly Lys Gly
    770                 775
```

<210> SEQ ID NO 33
<211> LENGTH: 45
<212> TYPE: DNA
<213> ORGANISM: Artificial Sequence
<220> FEATURE:
<223> OTHER INFORMATION: Designed oligonucleotide primer HT to amplify
      a genomic DNA of M13

<400> SEQUENCE: 33
ccggaaccgc ctccctcaga gccgccaccc tcagaaccgc caccc                45

<210> SEQ ID NO 34
<211> LENGTH: 38
<212> TYPE: DNA
<213> ORGANISM: Artificial Sequence
<220> FEATURE:
<223> OTHER INFORMATION: Designed oligonucleotide primer c280/RG34-F to
      amplify a genomic DNA of Thermus thermophilus HB-8

<400> SEQUENCE: 34
atatcatatg aaagaggcct tcaaggaggc cctcgccc                        38

<210> SEQ ID NO 35
<211> LENGTH: 40
<212> TYPE: DNA
<213> ORGANISM: Artificial Sequence
<220> FEATURE:
<223> OTHER INFORMATION: Designed oligonucleotide primer c280/RG34-R to
      amplify a genomic DNA of Thermus thermophilus HB-8

<400> SEQUENCE: 35
atatagatct ttattacgat ggccatacca acctcctgta                      40

<210> SEQ ID NO 36
<211> LENGTH: 38
<212> TYPE: DNA
<213> ORGANISM: Artificial Sequence
<220> FEATURE:
<223> OTHER INFORMATION: Designed oligonucleotide primer c240/RA18-F to
      amplify a genomic DNA of Thermus thermophilus HB-8

<400> SEQUENCE: 36
atatcatatg aaagtagagg aagtggttct tcccggcg                        38

<210> SEQ ID NO 37
<211> LENGTH: 40
<212> TYPE: DNA
<213> ORGANISM: Artificial Sequence
<220> FEATURE:
<223> OTHER INFORMATION: Designed oligonucleotide primer c240/RA18-R to
      amplify a genomic DNA of Thermus thermophilus HB-8

<400> SEQUENCE: 37

```
atatagatct ttattagaag ctccccttca gggcctccac                          40

<210> SEQ ID NO 38
<211> LENGTH: 35
<212> TYPE: DNA
<213> ORGANISM: Artificial Sequence
<220> FEATURE:
<223> OTHER INFORMATION: Designed oligonucleotide primer lambda-1B to
      amplify a lambda DNA

<400> SEQUENCE: 38
gatgagttcg tgtccgtaca actggcgtaa tcatg                               35

<210> SEQ ID NO 39
<211> LENGTH: 29
<212> TYPE: DNA
<213> ORGANISM: Artificial Sequence
<220> FEATURE:
<223> OTHER INFORMATION: Designed oligonucleotide primer lambda-9B to
      amplify a lambda DNA

<400> SEQUENCE: 39
tgtccgtcag ctcataacgg tacttcacg                                      29

<210> SEQ ID NO 40
<211> LENGTH: 28
<212> TYPE: DNA
<213> ORGANISM: Artificial Sequence
<220> FEATURE:
<223> OTHER INFORMATION: Designed oligonucleotide primer lambda-10D to
      amplify a lambda DNA

<400> SEQUENCE: 40
atatctggcg gtgcaatatc ggtactgt                                       28
```